(12) United States Patent
Hyde et al.

(10) Patent No.: US 9,897,995 B2
(45) Date of Patent: *Feb. 20, 2018

(54) POSITIONAL APPLICATOR DEVICE FOR USE WITH STRETCHABLE ELECTRONIC DEVICES AND RELATED METHODS

(71) Applicant: Elwha LLC, Bellevue, WA (US)

(72) Inventors: Roderick A. Hyde, Redmond, WA (US); Jordin T. Kare, San Jose, CA (US); Tony S. Pan, Bellevue, WA (US); Elizabeth L. Schubert, Bellevue, WA (US); Elizabeth A. Sweeney, Seattle, WA (US)

(73) Assignee: Elwha LLC, Bellevue, WA (US)

( * ) Notice: Subject to any disclaimer, the term of this patent is extended or adjusted under 35 U.S.C. 154(b) by 402 days.

This patent is subject to a terminal disclaimer.

(21) Appl. No.: 14/665,214

(22) Filed: Mar. 23, 2015

(65) Prior Publication Data

US 2016/0282836 A1 Sep. 29, 2016

(51) Int. Cl.
  *G05B 19/18* (2006.01)
  *A61M 5/00* (2006.01)
  *G05B 19/402* (2006.01)
  *A61M 5/172* (2006.01)

(52) U.S. Cl.
  CPC ......... *G05B 19/402* (2013.01); *A61M 5/1723* (2013.01); *A61M 2230/201* (2013.01); *G05B 2219/50047* (2013.01)

(58) Field of Classification Search
  CPC .......... A61M 2230/201; A61M 31/002; A61M 5/1723
  USPC ............................................... 700/56, 57, 58
  See application file for complete search history.

(56) References Cited

U.S. PATENT DOCUMENTS

| | | | |
|---|---|---|---|
| 8,097,926 B2 | 1/2012 | De Graff et al. | |
| 8,372,726 B2 | 2/2013 | de Graff et al. | |
| 8,536,667 B2 | 9/2013 | de Graff et al. | |
| 2006/0258939 A1 | 11/2006 | Pesach et al. | |
| 2007/0142619 A1 | 6/2007 | Hsu et al. | |
| 2011/0054583 A1 | 3/2011 | Litt et al. | |

(Continued)

OTHER PUBLICATIONS

PCT International Search Report; International App. No. PCT/US2016/034048; dated Jan. 10, 2017; pp. 1-3.

(Continued)

*Primary Examiner* — Michael J Brown

(57) ABSTRACT

Positional applicator devices and methods are for application of stretchable electronics relative to subsurface features of an object. In some embodiments, a positional applicator device for applying a stretchable electronic device to a surface of an object includes: a holder for a stretchable electronic device; a signal emitter positioned to direct an emitted signal toward a surface of an object; a receiver positioned to detect a return signal from the surface of the object; circuitry operably connected to the signal emitter and the receiver, the circuitry configured to compare the emitted signal with the return signal in order to identify surface and subsurface features of the object; circuitry configured to compare the identified features with a map of surface and subsurface features of the object stored in memory; and a positioner, the positioner structured to apply the stretchable electronic device to a position on the surface of the object.

38 Claims, 25 Drawing Sheets

(56) References Cited

U.S. PATENT DOCUMENTS

| | | | |
|---|---|---|---|
| 2012/0157804 A1 | 6/2012 | Rogers et al. | |
| 2012/0172715 A1* | 7/2012 | MacGregor | A61B 5/04085 600/424 |
| 2013/0041235 A1 | 2/2013 | Rogers et al. | |
| 2017/0007352 A1* | 1/2017 | King | A61B 90/90 |

OTHER PUBLICATIONS

Hwang et al.; "Materials and Fabrication Processes for Transient and Bioresorbable High-Performance Electronics"; Advanced Functional Materials; Apr. 11, 2013; pp. 4087-4093; vol. 23; Wiley-VCH Verlag GmbH & Co. KGaA, Weinheim.

Hwang et al.; "Materials for Bioresorbable Radio Frequency Electronics"; Advanced Materials; Feb. 27, 2013; pp. 1-6; Wiley-VCH Verlag GmbH & Co. KGaA, Weinheim.

Jeong et al.; "Materials and Optimized Designs for Human-Machine Interfaces Via Epidelinal Electronics"; Advanced Materials; Sep. 25, 2013; pp. 6839-6846; vol. 25; No. 47; Wiley-VCH Verlag GmbH & Co. KGaA, Weinheim.

Kim et al.; "Dissolvable Films of Silk Fibroin for Ultrathin, Conformal Bio-Integrated Electronics"; Nat Mater.; Jun. 2010; pp. 511-517; vol. 9, No. 6.

Kim et al.; "Epidermal Electronics"; Science; Aug. 12, 2011; pp. 838-843 and including attached Erratum; vol. 333; American Association for the Advancement of Science.

Kim et al.; "Materials for stretchable electronics in bioinspired and biointegrated devices"; MRS Bulletin; Mar. 2012; pp. 226-235; vol. 37; Materials Research Society.

Ma, Zhenqiang; "An Electronic Second Skin"; Science; Aug. 12, 2011; pp. 830-831; vol. 333; American Association for the Advancement of Science.

Salvatore et al.; "Wafer-scale design of lightweight and transparent electronics that wraps around hairs"; Nature Communications; Jan. 7, 2014; pp. 1-8; vol. 5; No. 2982; Macmillan Publishers Limited.

Swisher et al.; "Impedance sensing device enables early detection of pressure ulcers in vivo"; Nature Communications; Mar. 17, 2015; pp. 1-10; vol. 6; No. 6575; Macmillan Publishers Limited.

Yeo et al.; "Multifunctional Epidermal Electronics Printed Directly Onto the Skin"; Advanced Materials; Jan. 8, 2013; pp. 1-6; Wiley-VCH Verlag GmbH & Co. KGaA, Weinheim.

\* cited by examiner

FIG. 9

900 A method of applying a stretchable electronic device to a surface of an object 910 Initiating an emitted signal from a signal emitter, the emitted signal directed to a surface of an object 920 Detecting, with a receiver, a return signal from the emitted signal 930 Comparing, with circuitry, the emitted signal and the received return signal 940 Forming a representation of features of the object based on the comparison 950 Positioning a stretchable electronic device relative to the surface of the object in relation to the map 960 Applying the stretchable electronic device to the surface of the object

FIG. 10

1000 A method of applying a stretchable electronic device to a surface of an object 1010 Retaining a stretchable electronic device with a holder of a device 1020 Initiating an emitted signal from a signal emitter of the device, the emitted signal directed to a surface of an object 1030 Detecting, with a signal receiver of the device, a return signal from the emitted signal 1040 Comparing, with circuitry of the device, the emitted signal and the received return signal 1050 Forming, in circuitry of the device, a representation of features of the object based on the comparison 1060 Comparing, in circuitry of the device, a representation of features of the stretchable electronic device with the formed representation of features of the object based on the comparison 1070 Indicating, with a user interface of the device, a position for the stretchable electronic device relative to the surface of the object 1080 Applying the stretchable electronic device to the surface of the object

FIG. 11

1000 A method of applying a stretchable electronic device to a surface of an object

1010 Retaining a stretchable electronic device with a holder of a device

1020 Initiating an emitted signal from a signal emitter of the device, the signal directed to a surface of an object

1100 Initiating an optical signal directed to the surface of the object

1110 Initiating an ultrasound signal directed to the surface of the object

1030 Detecting, with a signal receiver of the device, a return signal from the emitted signal

1040 Comparing, with circuitry of the device, the emitted signal and the received return signal

1050 Forming, in circuitry of the device, a representation of features of the object based on the comparison

1060 Comparing, in circuitry of the device, a representation of features of the stretchable electronic device with the formed representation of features of the object based on the comparison

1070 Indicating, with a user interface of the device, a position for the stretchable electronic device relative to the surface of the object

1080 Applying the stretchable electronic device to the surface of the object

FIG. 12

1000 A method of applying a stretchable electronic device to a surface of an object

1010 Retaining a stretchable electronic device with a holder of a device

1020 Initiating an emitted signal from a signal emitter of the device, the emitted signal directed to a surface of an object

1200 Initiating a RF signal directed to the surface of the object

1210 Initiating an emitted signal from a signal emitter at a time to create a return signal from the surface of the object wherein the return signal is positioned to be received by the signal receiver of the device

1030 Detecting, with a signal receiver of the device, a return signal from the emitted signal

1040 Comparing, with circuitry of the device, the emitted signal and the received return signal

1050 Forming, in circuitry of the device, a representation of features of the object based on the comparison

1060 Comparing, in circuitry of the device, a representation of features of the stretchable electronic device with the formed representation of features of the object based on the comparison

1070 Indicating, with a user interface of the device, a position for the stretchable electronic device relative to the surface of the object

1080 Applying the stretchable electronic device to the surface of the object

FIG. 13

1000 A method of applying a stretchable electronic device to a surface of an object

1010 Retaining a stretchable electronic device with a holder of a device

1020 Initiating an emitted signal from a signal emitter of the device, the emitted signal directed to a surface of an object

1030 Detecting, with a signal receiver of the device, a return signal from the emitted signal > 1300 Detecting an optical signal directed from the surface of the object > 1310 Detecting an ultrasound signal directed from the surface of the object > 1320 Detecting an RF signal directed from the surface of the object

1040 Comparing, with circuitry of the device, the emitted signal and the received return signal

1050 Forming, in circuitry of the device, a representation of features of the object based on the comparison

1060 Comparing, in circuitry of the device, a representation of features of the stretchable electronic device with the formed representation of features of the object based on the comparison

1070 Indicating, with a user interface of the device, a position for the stretchable electronic device relative to the surface of the object

1080 Applying the stretchable electronic device to the surface of the object

FIG. 14

1000 A method of applying a stretchable electronic device to a surface of an object

1010 Retaining a stretchable electronic device with a holder of a device

1020 Initiating an emitted signal from a signal emitter of the device, the emitted signal directed to a surface of an object

1030 Detecting, with a signal receiver of the device, a return signal from the emitted signal

1040 Comparing, with circuitry of the device, the emitted signal and the received return signal > 1400 Forming, in circuitry of the device, a representation of features of the object; and
> Comparing, in circuitry of the device, the representation of features of the object with a representation of features of the stretchable electronic device

1050 Forming, in circuitry of the device, a representation of features of the object based on the comparison

1060 Comparing, in circuitry of the device, a representation of features of the stretchable electronic device with the formed representation of features of the object based on the comparison

1070 Indicating, with a user interface of the device, a position for the stretchable electronic device relative to the surface of the object

1080 Applying the stretchable electronic device to the surface of the object

FIG. 15

1000 A method of applying a stretchable electronic device to a surface of an object > 1010 Retaining a stretchable electronic device with a holder of a device > 1020 Initiating an emitted signal from a signal emitter of the device, the emitted signal directed to a surface of an object > 1030 Detecting, with a signal receiver of the device, a return signal from the emitted signal > 1040 Comparing, with circuitry of the device, the emitted signal and the received return signal > 1050 Forming, in circuitry of the device, a representation of features of the object based on the comparison
>
>> 1500 Providing, from electronic memory of the device, information regarding features of the object
>
>> 1510 Providing, from electronic memory of the device, information regarding at least one prior stretchable electronic device that was previously affixed to the surface > 1060 Comparing, in circuitry of the device, a representation of features of the stretchable electronic device with the formed representation of features of the object based on the comparison > 1070 Indicating, with a user interface of the device, a position for the stretchable electronic device relative to the surface of the object > 1080 Applying the stretchable electronic device to the surface of the object

FIG. 16

1000 A method of applying a stretchable electronic device to a surface of an object

1010 Retaining a stretchable electronic device with a holder of a device

1020 Initiating an emitted signal from a signal emitter of the device, the emitted signal directed to a surface of an object

1030 Detecting, with a signal receiver of the device, a return signal from the emitted signal

1040 Comparing, with circuitry of the device, the emitted signal and the received return signal

1050 Forming, in circuitry of the device, a representation of features of the object based on the comparison

1060 Comparing, in circuitry of the device, a representation of features of the stretchable electronic device with the formed representation of features of the object based on the comparison > 1600 Providing, from electronic memory of the device, information regarding features of the stretchable electronic device

1070 Indicating, with a user interface of the device, a position for the stretchable electronic device relative to the surface of the object

1080 Applying the stretchable electronic device to the surface of the object

FIG. 17

1000 A method of applying a stretchable electronic device to a surface of an object 1010 Retaining a stretchable electronic device with a holder of a device 1020 Initiating an emitted signal from a signal emitter of the device, the emitted signal directed to a surface of an object 1030 Detecting, with a signal receiver of the device, a return signal from the emitted signal 1040 Comparing, with circuitry of the device, the emitted signal and the received return signal 1050 Forming, in circuitry of the device, a representation of features of the object based on the comparison 1060 Comparing, in circuitry of the device, a representation of features of the stretchable electronic device with the formed representation of features of the object based on the comparison 1070 Indicating, with a user interface of the device, a position for the stretchable electronic device relative to the surface of the object 1700 Indicating on a visual representation of the user interface 1710 Initiating a signal from a sound emitter 1720 Emitting a light pattern in a direction to the surface of the object from a light emitter of the device, the light pattern of a size and shape to indicate a position of the device to a user 1080 Applying the stretchable electronic device to the surface of the object

FIG. 18

| 1000 A method of applying a stretchable electronic device to a surface of an object |
|---|

| 1010 Retaining a stretchable electronic device with a holder of a device |
|---|

| 1020 Initiating an emitted signal from a signal emitter of the device, the emitted signal directed to a surface of an object |
|---|

| 1030 Detecting, with a signal receiver of the device, a return signal from the emitted signal |
|---|

| 1040 Comparing, with circuitry of the device, the emitted signal and the received return signal |
|---|

| 1050 Forming, in circuitry of the device, a representation of features of the object based on the comparison |
|---|

| 1060 Comparing, in circuitry of the device, a representation of features of the stretchable electronic device with the formed representation of features of the object based on the comparison |
|---|

| 1070 Indicating, with a user interface of the device, a position for the stretchable electronic device relative to the surface of the object |
|---|
| 1800 Indicating that a user should not move the stretchable electronic device relative to the surface of the object |
| 1810 Indicating a direction that a user should move the stretchable electronic device relative to the surface of the object |
| 1820 Indicating a distance that a user should move the stretchable electronic device relative to the surface of the object |

| 1080 Applying the stretchable electronic device to the surface of the object |
|---|

FIG. 19

1000 A method of applying a stretchable electronic device to a surface of an object

1010 Retaining a stretchable electronic device with a holder of a device

1020 Initiating an emitted signal from a signal emitter of the device, the emitted signal directed to a surface of an object

1030 Detecting, with a signal receiver of the device, a return signal from the emitted signal

1040 Comparing, with circuitry of the device, the emitted signal and the received return signal

1050 Forming, in circuitry of the device, a representation of features of the object based on the comparison

1060 Comparing, in circuitry of the device, a representation of features of the stretchable electronic device with the formed representation of features of the object based on the comparison

1070 Indicating, with a user interface of the device, a position for the stretchable electronic device relative to the surface of the object > 1900 Indicating a rotation direction that a user should move the stretchable electronic device relative to the surface of the object > 1910 Indicating a rotation amount that a user should move the stretchable electronic device relative to the surface of the object

1080 Applying the stretchable electronic device to the surface of the object

FIG. 20

1000 A method of applying a stretchable electronic device to a surface of an object

1010 Retaining a stretchable electronic device with a holder of a device

1020 Initiating an emitted signal from a signal emitter of the device, the emitted signal directed to a surface of an object

1030 Detecting, with a signal receiver of the device, a return signal from the emitted signal

1040 Comparing, with circuitry of the device, the emitted signal and the received return signal

1050 Forming, in circuitry of the device, a representation of features of the object based on the comparison

1060 Comparing, in circuitry of the device, a representation of features of the stretchable electronic device with the formed representation of features of the object based on the comparison

1070 Indicating, with a user interface of the device, a position for the stretchable electronic device relative to the surface of the object

1080 Applying the stretchable electronic device to the surface of the object > 2000 Applying tension to the stretchable electronic device from an adaptable tensioner in response to the controller > 2010 Positioning a surface of the stretchable electronic device against the surface of the object

FIG. 21

1000 A method of applying a stretchable electronic device to a surface of an object

1010 Retaining a stretchable electronic device with a holder of a device

1020 Initiating an emitted signal from a signal emitter of the device, the emitted signal directed to a surface of an object

1030 Detecting, with a signal receiver of the device, a return signal from the emitted signal

1040 Comparing, with circuitry of the device, the emitted signal and the received return signal

1050 Forming, in circuitry of the device, a representation of features of the object based on the comparison

1060 Comparing, in circuitry of the device, a representation of features of the stretchable electronic device with the formed representation of features of the object based on the comparison

1070 Indicating, with a user interface of the device, a position for the stretchable electronic device relative to the surface of the object

1080 Applying the stretchable electronic device to the surface of the object

2100 Storing, in electronic memory, data from the detected signal

2110 Storing, in electronic memory, information regarding features of the object

2120 Detecting, with an accelerometer of the device, a motion of the device; and
indicating, with a user interface of the device, in response to the motion of the device

FIG. 22

1000 A method of applying a stretchable electronic device to a surface of an object 1010 Retaining a stretchable electronic device with a holder of a device 1020 Initiating an emitted signal from a signal emitter of the device, the emitted signal directed to a surface of an object 1030 Detecting, with a signal receiver of the device, a return signal from the emitted signal 1040 Comparing, with circuitry of the device, the emitted signal and the received return signal 1050 Forming, in circuitry of the device, a representation of features of the object based on the comparison 1060 Comparing, in circuitry of the device, a representation of features of the stretchable electronic device with the formed representation of features of the object based on the comparison 1070 Indicating, with a user interface of the device, a position for the stretchable electronic device relative to the surface of the object 1080 Applying the stretchable electronic device to the surface of the object 2200 Spraying the surface of the object with an adhesive formulated to adhere a surface of the stretchable electronic device to the surface of the object 2210 Selecting a portion of the surface of the object in response to the representation of features of the object; and removing the portion of the surface of the object with an abrader of the device

FIG. 23

1000 A method of applying a stretchable electronic device to a surface of an object 1010 Retaining a stretchable electronic device with a holder of a device 1020 Initiating an emitted signal from a signal emitter of the device, the emitted signal directed to a surface of an object 1030 Detecting, with a signal receiver of the device, a return signal from the emitted signal 1040 Comparing, with circuitry of the device, the emitted signal and the received return signal 1050 Forming, in circuitry of the device, a representation of features of the object based on the comparison 1060 Comparing, in circuitry of the device, a representation of features of the stretchable electronic device with the formed representation of features of the object based on the comparison 1070 Indicating, with a user interface of the device, a position for the stretchable electronic device relative to the surface of the object 1080 Applying the stretchable electronic device to the surface of the object 2300 Determining a light pattern to project on the surface of the object relative to the position of the device; and projecting the light pattern on the surface of the object 2310 Emitting a verbal signal in response to the controller

FIG. 24

2400 A method of applying a stretchable electronic device to a surface of a body region 2410 Retaining a stretchable electronic device with a holder of a device 2420 Initiating an emitted signal from a signal emitter of the device, the emitted signal directed to a surface of a body region 2430 Detecting, with a signal receiver of the device, a return signal from the emitted signal 2440 Comparing, with circuitry of the device, the emitted signal and the received return signal 2450 Forming, in circuitry of the device, a representation of features of the body region based on the comparison 2460 Comparing, in circuitry of the device, a representation of features of the stretchable electronic device with the formed representation of features of the body region based on the comparison 2470 Indicating, with a user interface of the device, a position for the stretchable electronic device relative to the surface of the body region 2480 Applying the stretchable electronic device to the surface of the body region

FIG. 25

2500 A method of applying a stretchable electronic device to a surface of an inanimate object 2510 Retaining a stretchable electronic device with a holder of a device 2520 Initiating an emitted signal from a signal emitter of the device, the emittedsignal directed to a surface of an inanimate object 2530 Detecting, with a signal receiver of the device, a return signal from the emitted signal 2540 Comparing, with circuitry of the device, the emitted signal and the received return signal 2550 Forming, in circuitry of the device, a representation of features of the inanimate object based on the comparison 2560 Comparing, in circuitry of the device, a representation of features of the stretchable electronic device with the formed representation of features of the inanimate object based on the comparison 2570 Indicating, with a user interface of the device, a position for the stretchable electronic device relative to the surface of the inanimate object 2580 Applying the stretchable electronic device to the surface of the inanimate object

POSITIONAL APPLICATOR DEVICE FOR USE WITH STRETCHABLE ELECTRONIC DEVICES AND RELATED METHODS If an Application Data Sheet (ADS) has been filed on the filing date of this application, it is incorporated herein by reference. Any applications claimed on the ADS for priority under 35 U.S.C. §§ 119, 120, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

CROSS-REFERENCE TO RELATED APPLICATIONS

The present application claims the benefit of the earliest available effective filing date(s) from the following listed application(s) (the "Priority Applications"), if any, listed below (e.g., claims earliest available priority dates for other than provisional patent applications or claims benefits under 35 USC §119(e) for provisional patent applications, for any and all parent, grandparent, great-grandparent, etc. applications of the Priority Application(s)).

PRIORITY APPLICATIONS

None.

If the listings of applications provided above are inconsistent with the listings provided via an ADS, it is the intent of the Applicant to claim priority to each application that appears in the Domestic Benefit/National Stage Information section of the ADS and to each application that appears in the Priority Applications section of this application.

All subject matter of the Priority Applications and of any and all applications related to the Priority Applications by priority claims (directly or indirectly), including any priority claims made and subject matter incorporated by reference therein as of the filing date of the instant application, is incorporated herein by reference to the extent such subject matter is not inconsistent herewith.

SUMMARY

In some embodiments, a positional applicator device for applying a stretchable electronic device to a surface of an object includes: a holder for a stretchable electronic device; a signal emitter positioned to direct an emitted signal toward a surface of an object; a receiver positioned to detect a return signal from the surface of the object; circuitry operably connected to the signal emitter and the receiver, the circuitry configured to compare the emitted signal with the return signal in order to identify surface and subsurface features of the object; circuitry configured to compare the identified surface and subsurface features with a map of surface and subsurface features of the object stored in memory; and a positioner operably affixed to the holder, the positioner positioned and structured to apply the stretchable electronic device to a position on the surface of the object based on, or using information from, the comparison.

In some embodiments, a positional applicator device for applying a stretchable electronic device to a surface of an object includes: a holder for a stretchable electronic device; a signal emitter positioned to direct an emitted signal toward a surface of an object; a signal receiver positioned to detect a return signal from the surface of the object, the return signal originating with the emitted signal directed from the signal emitter; a controller including circuitry operably connected to the signal emitter and to the signal receiver, the circuitry configured to compare the emitted signal with the return signal to form a representation of features of the object, and circuitry configured to compare the representation of features of the object with a representation of features of the stretchable electronic device; a user interface operably attached to the controller; a positioner operably affixed to the holder, the positioner positioned and structured to apply, in response to the controller, the stretchable electronic device to a position on the surface of the object relative to the representation of features of the object and the representation of features of the stretchable electronic device; and an applicator of a size and shape to place the stretchable electronic device in contact with the surface of the object, the applicator including a switch operably attached to the controller.

In some embodiments, a positional applicator device for applying a stretchable electronic device to a surface of a body region includes: a holder for a stretchable electronic device; a signal emitter positioned to direct an emitted signal toward a surface of a body region; a signal receiver positioned to detect a return signal from the surface, the return signal originating with the emitted signal directed from the signal emitter; a controller including circuitry operably connected to the signal emitter and the signal receiver, the circuitry configured to compare the emitted signal with the return signal to form a representation of features of the body region, and circuitry configured to compare the representation of features of the body region with a representation of features of the stretchable electronic device; a user interface operably attached to the controller; a positioner operably affixed to the holder, the positioner positioned and structured to apply, in response to the controller, the stretchable electronic device to a position on the surface of the body region based on, or using information from, the representation of features of the body region and the representation of features of the stretchable electronic device; and an applicator of a size and shape to place the stretchable electronic device in contact with the surface of the body region, the applicator including a switch operably attached to the controller.

In some embodiments, a positional applicator device for applying a stretchable electronic device to a surface of an inanimate object includes: a holder for a stretchable electronic device; a signal emitter positioned to direct an emitted signal toward a surface of an inanimate object; a signal receiver positioned to detect a return signal from the surface, the return signal originating with the emitted signal directed from the signal emitter; a controller including circuitry operably connected to the signal emitter and the signal receiver, the circuitry configured to compare the emitted signal with the return signal to form a representation of features of the inanimate object, and circuitry configured to compare the representation of features of the inanimate object with a representation of features of the stretchable electronic device; a user interface operably attached to the controller; a positioner operably affixed to the holder, the positioner positioned and structured to apply, in response to the controller, the stretchable electronic device to a position on the surface of the inanimate object based on, or using information from, the representation of features of the inanimate object and the representation of features of the stretchable electronic device; and an applicator of a size and shape to place the stretchable electronic device in contact with the surface of the inanimate object, the applicator including a switch operably attached to the controller.

In some embodiments, a positional applicator device for applying a stretchable electronic device to a surface of an object includes: a holder for a stretchable electronic device; a signal emitter positioned to direct an emitted signal toward a surface of an object; a signal receiver positioned to detect a return signal from the surface, the return signal originating with the emitted signal directed from the signal emitter; a controller including circuitry operably connected to the signal emitter and the signal receiver, the circuitry configured to compare the emitted signal with the return signal to form a representation of features of the object, and circuitry configured to compare the representation of features of the object with a representation of features of the stretchable electronic device; a positioner operably affixed to the holder, the positioner positioned and structured to apply, in response to the controller, the stretchable electronic device to a position on the surface of the object based on, or using information from, the representation of features of the object and the representation of features of the stretchable electronic device; a stabilizer of a size and shape to stabilize the surface of the object relative to the positioner; and an applicator of a size and shape to place the stretchable electronic device in contact with the surface of the object, the applicator including a switch operably attached to the controller.

In some embodiments, a positional applicator device for applying a stretchable electronic device to a surface of a body region includes: a holder for a stretchable electronic device; a signal emitter positioned to direct an emitted signal toward a surface of a body region; a signal receiver positioned to detect a return signal from the surface, the return signal originating with the emitted signal directed from the signal emitter; a controller including circuitry operably connected to the signal emitter and the signal receiver, the circuitry configured to compare the emitted signal with the return signal to form a representation of features of the body region, and circuitry configured to compare the representation of features of the body region with a representation of features of the stretchable electronic device; a positioner operably affixed to the holder, the positioner positioned and structured to apply, in response to the controller, the stretchable electronic device to a position on the surface of the body region based on, or using information from, the representation of features of the body region and the representation of features of the stretchable electronic device; a stabilizer of a size and shape to stabilize the surface of the body region relative to the positioner; and an applicator of a size and shape to place the stretchable electronic device in contact with the surface of the body region, the applicator including a switch operably attached to the controller.

In some embodiments, a method of applying a stretchable electronic device to a surface of an object includes: initiating an emitted signal from a signal emitter, the emitted signal directed to a surface of an object; detecting, with a receiver, a return signal from the emitted signal; comparing, with circuitry, the emitted signal and the received return signal; forming a representation of features of the object based on, or using information from, the comparison; and positioning a stretchable electronic device relative to the surface of the object in relation to the map.

In some embodiments, a method of applying a stretchable electronic device to a surface of an object includes: retaining a stretchable electronic device with a holder of a positional applicator device; initiating an emitted signal from a signal emitter of the positional applicator device, the emitted signal directed to a surface of an object; detecting, with a signal receiver of the positional applicator device, a return signal from the emitted signal; comparing, with circuitry of the positional applicator device, the emitted signal and the received return signal; forming, in circuitry of the positional applicator device, a representation of features of the object based on the comparison; comparing, in circuitry of the positional applicator device, a representation of features of the stretchable electronic device with the formed representation of features of the object based on the comparison; indicating, with a user interface of the positional applicator device, a position for the stretchable electronic device relative to the surface of the object; and applying the stretchable electronic device to the surface of the object.

In some embodiments, a method of applying a stretchable electronic device to a surface of a body region includes: retaining a stretchable electronic device with a holder of a positional applicator device; initiating an emitted signal from a signal emitter of the positional applicator device, the emitted signal directed to a surface of a body region; detecting, with a signal receiver of the positional applicator device, a return signal from the emitted signal; comparing, with circuitry of the positional applicator device, the emitted signal and the received return signal; forming, in circuitry of the positional applicator device, a representation of features of the body region based on the comparison; indicating, with a user interface of the positional applicator device, a position for the stretchable electronic device relative to the surface of the body region; and applying the stretchable electronic device to the surface of the body region.

In some embodiments, a method of applying a stretchable electronic device to a surface of an inanimate object includes: retaining a stretchable electronic device with a holder of a positional applicator device; initiating an emitted signal from a signal emitter of the positional applicator device, the emitted signal directed to a surface of an inanimate object; detecting, with a signal receiver of the positional applicator device, a return signal from the emitted signal; comparing, with circuitry of the positional applicator device, the emitted signal and the received return signal; forming, in circuitry of the positional applicator device, a representation of features of the inanimate object based on the comparison; indicating, with a user interface of the positional applicator device, a position for the stretchable electronic device relative to the surface of the inanimate object; and applying the stretchable electronic device to the surface of the inanimate object.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIG. 9 is a flowchart of a method.

FIG. 10 is a flowchart of a method.

FIG. 11 is a flowchart showing aspects of the method of FIG. 10.

FIG. 12 is a flowchart showing aspects of the method of FIG. 10.

FIG. 13 is a flowchart showing aspects of the method of FIG. 10.

FIG. 14 is a flowchart showing aspects of the method of FIG. 10.

FIG. 15 is a flowchart showing aspects of the method of FIG. 10.

FIG. 16 is a flowchart showing aspects of the method of FIG. 10.

FIG. 17 is a flowchart showing aspects of the method of FIG. 10.

FIG. 18 is a flowchart showing aspects of the method of FIG. 10.

FIG. 19 is a flowchart showing aspects of the method of FIG. 10.

FIG. 20 is a flowchart showing aspects of the method of FIG. 10.

FIG. 21 is a flowchart showing aspects of the method of FIG. 10.

FIG. 22 is a flowchart showing aspects of the method of FIG. 10.

FIG. 23 is a flowchart showing aspects of the method of FIG. 10.

FIG. 24 is a flowchart of a method.

FIG. 25 is a flowchart of a method.

DETAILED DESCRIPTION

Figure 1:
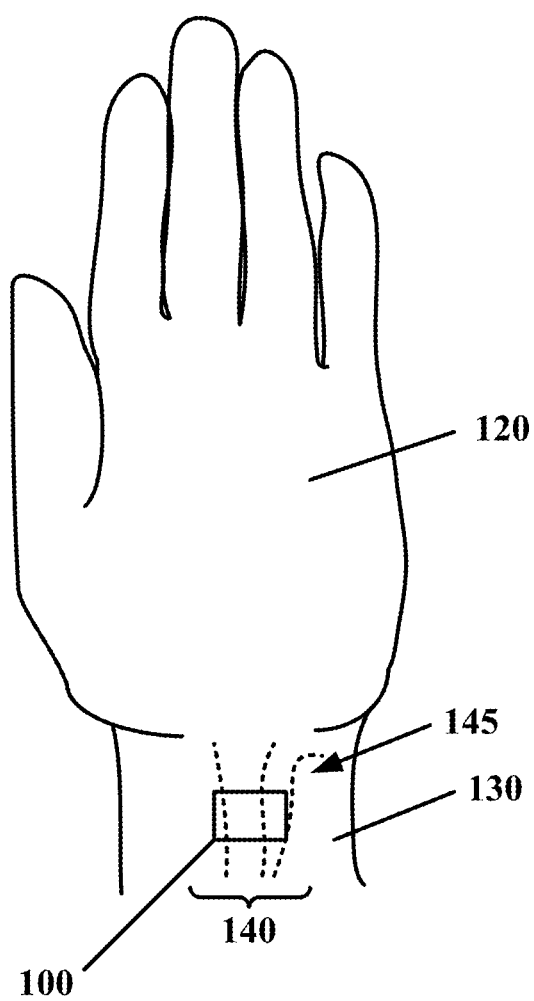
FIG. 1 is a schematic of a body part with an affixed stretchable electronic device.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

In some situations, the performance and/or operation of a stretchable electronic device worn on the body depends in part on the specific orientation and position of the stretchable electronic device on the surface of the body part relative to one or more features underlying the surface of the body part. For example, in some embodiments, a stretchable electronic device is placed on a body part in order to monitor an internal condition of the body, such as blood pressure, pulse, nerve activity, muscle activity, and/or motion of internal structures. Precise positioning and orientation of the stretchable electronic device can improve the ability of the device to carry out this monitoring. See, e.g., Jeong et al., "Materials and Optimized Designs for Human-Machine Interfaces Via Epidermal Electronics," *Advanced Materials* 25: 6839-6846 (2013), which is incorporated by reference. For example, a stretchable electronic device can include a sensor of electrical activity at a specific location on the electronic device, and position of that sensor adjacent to a subsurface nerve can improve the detection of electrical activity in that particular nerve. For example, a stretchable electronic device can include an antenna and be configured to accept signals from an implanted medical device within a body, and to relay the received signals from the implant to an external device distal to the body. The position and orientation of the stretchable electronic device and its antenna can, in some situations, impact the functionality of the antenna and the relay of signals from the implant to an external device distal to the body. Similarly, a stretchable electronic device can include an inductive coil and be positioned and oriented to provide power to an implant located in a subsurface position in a body. For example, a stretchable electronic device can include a heater and a thermocouple, and the stretchable electronic device can be configured to detect temperature of the object and then to deliver heat to the object. For example, a stretchable electronic device can include an RFID tag which is intended to be placed at a position or orientation relative to the object. Devices and methods described herein can be used to assist with the positioning and orientation of one or more stretchable electronic devices during application to a surface of a body relative to subsurface features.

In some situations, the performance and/or operation of a stretchable electronic device affixed to a surface of an inanimate object depends in part on the specific orientation and position of the stretchable electronic device on the surface of the inanimate object relative to one or more features underlying the surface of the inanimate object. For example, in some embodiments, a stretchable electronic device is placed on an inanimate object in order to monitor an internal condition of the inanimate object, such as electrical activity, magnetic activity, sound, internal motion, and/or structural integrity of material. Precise positioning and orientation of the stretchable electronic device can improve the ability of the device to carry out this monitoring. For example, a stretchable electronic device can include a motion sensor, and positioning of the motion sensor adjacent to a motor within the inanimate object can improve detection of motion of the motor. For example, a stretchable electronic device can include an electrical sensor, and positioning of the electrical sensor adjacent to an electrical conduit within the inanimate object can improve detection of electrical signals from the conduit. For example, a stretchable electronic device can include a thermocouple or a radiator, and the stretchable electronic device can be configured to detect heat and then to disperse the heat along the surface of the object or transfer it to external air. The position and orientation of the thermocouple or radiator can, in some situations, alter the ability of the stretchable electronic device to detect and disperse heat along the surface of the object. Devices and methods described herein can be used to assist with the positioning and orientation of one or more stretchable electronic devices during application to a surface of an inanimate object relative to subsurface features.

With reference now to FIG. 1, shown is an example of a stretchable electronic device affixed to a human wrist that may serve as a context for introducing one or more processes and/or devices described herein. The use of the same symbols in different drawings typically indicates similar or identical items unless context dictates otherwise. Aspects of the figures are portrayed for purposes of illustration, and accordingly may not be drawn to scale. FIG. 1 depicts an embodiment wherein a stretchable electronic device is applied to a specific location on a surface, and orientation on the surface, relative to the underlying features underneath that specific surface. FIG. 1 depicts a stretchable electronic device affixed to a human wrist relative to, inter alia, the blood vessels underlying the skin surface of the wrist.

Although a particular configuration of blood vessels is illustrated in FIG. 1, the precise positioning of blood vessels in a particular human wrist varies between individuals. The features of a human body underlying the surface, such as blood vessel position, may be partially visible or not visible, depending on the individual person and their position at a particular time. In addition, other features of a human body underlying the skin layer will vary between individuals, such as the size of a body part, the curvature and surface of the body part, and the composition and precise position of the underlying features of the body part. Therefore, the exact positioning and orientation of a stretchable electronic device will vary between individuals.

Some embodiments of the devices and methods are suitable for use to apply a stretchable electronic device to the surface of an inanimate object, the stretchable electronic device positioned and oriented relative to underlying features of the surface. For example, in some embodiments a stretchable electronic device can be applied to a surface of another device relative to features such as cracks, voids or gaps in the structure underlying the surface, anticipated stress concentration sites, electric connections under the surface, motors within the inanimate object, or other features within the inanimate object. Therefore, the exact positioning and orientation of a stretchable electronic device relative to features under the surface can vary between specific inanimate objects that are otherwise similar.

Some embodiments of the devices and methods are suitable for use to apply a stretchable electronic device to the surface of a plant, the stretchable electronic device positioned and oriented relative to underlying features of the surface. For example, in some embodiments a stretchable electronic device can be applied to a surface of a plant relative to features such as pores, internal channels, internal cavities, buds, branch points, or other features within the plant. Therefore, the exact positioning and orientation of a stretchable electronic device relative to features under the surface can vary between specific plants that are otherwise similar.

FIG. 1 illustrates a human hand 120 and wrist 130 regions of a body. The wrist 130 includes a region of interest 140 which includes a plurality of blood vessels 145 under the skin, and adjacent to the skin layer. Although blood vessels 145 are illustrated in FIG. 1, similarly situated blood vessels may or may not be visible in a given individual depending on factors such as skin thickness and pigmentation of an individual. A stretchable electronic device 100 is affixed to the wrist 130 in the region of interest 140. In some embodiments, the stretchable electronic device can be of a type and positioned to monitor different aspects of the underlying features of the adjacent surface. For example, in embodiments wherein a stretchable electronic device is affixed to a surface of a body part, the stretchable electronic device may be positioned and oriented relative to features under the surface such as blood vessels, nerves, bones, fat deposits, muscle groups, skin layer thickness and composition, and prior surgical implants. The features under the surface may not be visible to a user. See, e.g. Swisher et al., "Impedance Sensing Device Enables Early Detection of Pressure Ulcers in Vivo", Nature Communications, 6: 6575, doi: 10/1038.ncomms7575, which is incorporated herein by reference. In addition, a stretchable electronic device can be positioned and oriented relative to features that are included at the surface level, such as scar tissue, wrinkles, tattoos, pigmented regions, neoplastic regions, and wear regions. Features that are included at the surface level may not be easily visible to a user. A stretchable electronic device can also be positioned and oriented on a body part relative to cosmetic or comfort desires of the wearer.

A "stretchable electronic device," as used herein, includes a flexible and stretchable substrate and attached electronic circuitry, the device fabricated as an extremely thin structure of a size and shape to conform with a surface of an object for a period of time, such as days or weeks. In some embodiments, a stretchable electronic device has a thickness on in the μm scale, and has a low Young's modulus, on the kPa scale (see, e.g. Kim et al., "Epidermal Electronics," Science 333: 838-843, (2011), which is incorporated herein by reference). For example, in some embodiments a stretchable electronic device has an average thickness less than 100 μm, and an average Young's modulus less than 100 kPa. For example, in some embodiments a stretchable electronic device has an average thickness less than 50 μm, and an average Young's modulus less than 80 kPa. For example, in some embodiments a stretchable electronic device has an average thickness less than 500 microns, and an average modulus less than or equal to 500 kPa (see, e.g. US Patent Application Publication No. 2013/0041235, "Flexible and Stretchable Electronic Systems for Epidermal Electronics, to Rodgers and Kim, which is incorporated herein by reference). In some embodiments, a stretchable electronic device can be an epidermal electronic device (see, e.g. Kim et al., "Epidermal Electronics," Science 333: 838-843, (2011), and Ma, "An Electronic Second Skin," Science 333: 830-831, (2011), which are each incorporated herein by reference). In some embodiments, a stretchable electronic device can be a conformal electronic device. In some embodiments, a stretchable electronic device includes a support fabricated from silk fibroin (see, e.g. Kim et al., "Dissolvable Films of Silk Fibroin for Ultrathin, Conformal Bio-Integrated Electronics," Nature Materials 9(6): 511-517 (2010), which is incorporated herein by reference). Some embodiments include a stretchable electronic device from a support, which can include a support that is peeled off or dissolved away after application of the stretchable electronic device to the surface (see, e.g.: Yeo et al., "Multifunctional Epidermal Electronics Printed Directly Onto the Skin," Advanced Materials (2013), DOI: 10.1002/adma.201204426; US Patent Application Publication No. 2012/0157804, "High-speed, High-resolution Electrophysiology In-vivo Using Conformal Electronics" to Rogers et al.; Salvatore et al., "Wafer-scale Design of Lightweight and Transparent Electronics that Wraps Around Hairs," Nature Communications (2014) DOI: 10.1038/ncomms3982; and US Patent Application Publication No. 2013/0041235, "Flexible and Stretchable Electronic Systems for Epidermal Electronics, to Rodgers and Kim, which are each incorporated herein by reference). Some embodiments include a stretchable electronic device including a barrier layer. The barrier layer of a stretchable electronic device can include patterns to modulate contact between one or more features of the stretchable electronic device and a surface affixed to the stretchable electronic device (see, e.g., US Patent Application Publication No. 2012/0157804, "High-speed, High-resolution Electrophysiology In-vivo Using Conformal Electronics" to Rogers et al., which is incorporated herein by reference).

A stretchable electronic device can include a plurality of inflexible blocks, sometimes referred to as device islands, each affixed to a support and integrated into a stretchable electronic device (see, e.g.: US Patent Application Publication No. 2013/0041235, "Flexible and Stretchable Electronic Systems for Epidermal Electronics, to Rodgers; U.S. Pat. No. 8,536,667, "Systems, Methods and Devices Having Stretchable Integrated Circuitry for Sensing and Delivering Therapy," to de Graff et al; U.S. Pat. No. 8,097,926, "Systems, Methods and Devices Having Stretchable Integrated Circuitry for Sensing and Delivering Therapy," to de Graff et al; and Kim, and Kim et al., "Materials for Stretchable Electronics in Bioinspired and Biointegrated Devices," *MRS Bulletin* 37: 226-235 (2012), which are each incorporated herein by reference). In some embodiments, each of the inflexible blocks includes a functional unit. For example, a functional unit can include a temperature sensor, a pressure sensor, an accelerometer, antenna, receiver, transmitter, electrical sensor, magnetic sensor, tension sensor, processor, energy harvesting device, circuitry to any of the functional units, or other functional component. The inflexible blocks including functional units can be connected to each other by wire connectors to create electrical circuitry system throughout the stretchable electronic device. The inflexible blocks including functional units can be connected to each other by wireless connectors to create electrical circuitry system throughout the stretchable electronic device. See, e.g. US Patent Application Publication No. 2011/0054583, "Flexible and Scalable Sensor Arrays for Recording and Modulating Physiologic Activity," to Litt and Viventi, which is incorporated herein by reference. In some embodiments, a stretchable electronic device can be fabricated by use of a stamp (see, e.g.: US Patent Application Publication No. 2007/0142619, "Forming Electrical Contacts to a Molecular Layer," to Hsu et al.; and U.S. Pat. No. 8,372,726, "Methods and Applications of Non-planar Imaging Arrays," to de Graff et al., which are each incorporated herein by reference).

In some embodiments, a stretchable electronic device can be fabricated with a silicon wafer substrate (see, e.g., Hwang et al., "Materials and Fabrication Processes for Transient and Bioresorbable High-performance Electronics," *Advanced Materials* (2013), DOI: 10.1002/adfm.201300127, which is incorporated herein by reference). In some embodiments, a stretchable electronic device can be fabricated to include bioresorbable radio frequency electronics (see, e.g, Hwang et al., "Materials for Bioresorbable Radio Frequency Electronics," *Advanced Materials* (2013), DOI: 10.1002/adma.201300920, which is incorporated herein by reference).

A "user," as used herein, is a person applying a stretchable electronic device to a surface. In embodiments wherein the stretchable electronic device is applied to the surface of a body part (e.g. the skin or epithelial tissue), the user can include a medical team member applying the stretchable electronic device. In some embodiments, devices and methods as described herein can be used by an individual to apply a stretchable electronic device to their own body surface(s) relative to features underlying the surface, and a "user" can include the individual. In some embodiments, a stretchable electronic device is applied to the surface of an inanimate object, and the user is the person who carries out the application relative to features underlying the surface of the object. Depending on the embodiment, a user can be representative of a human user, a robotic user (e.g., computational entity), and/or substantially any combination thereof (e.g., a user may be assisted by one or more robotic agents) unless context dictates otherwise.

Figure 2:
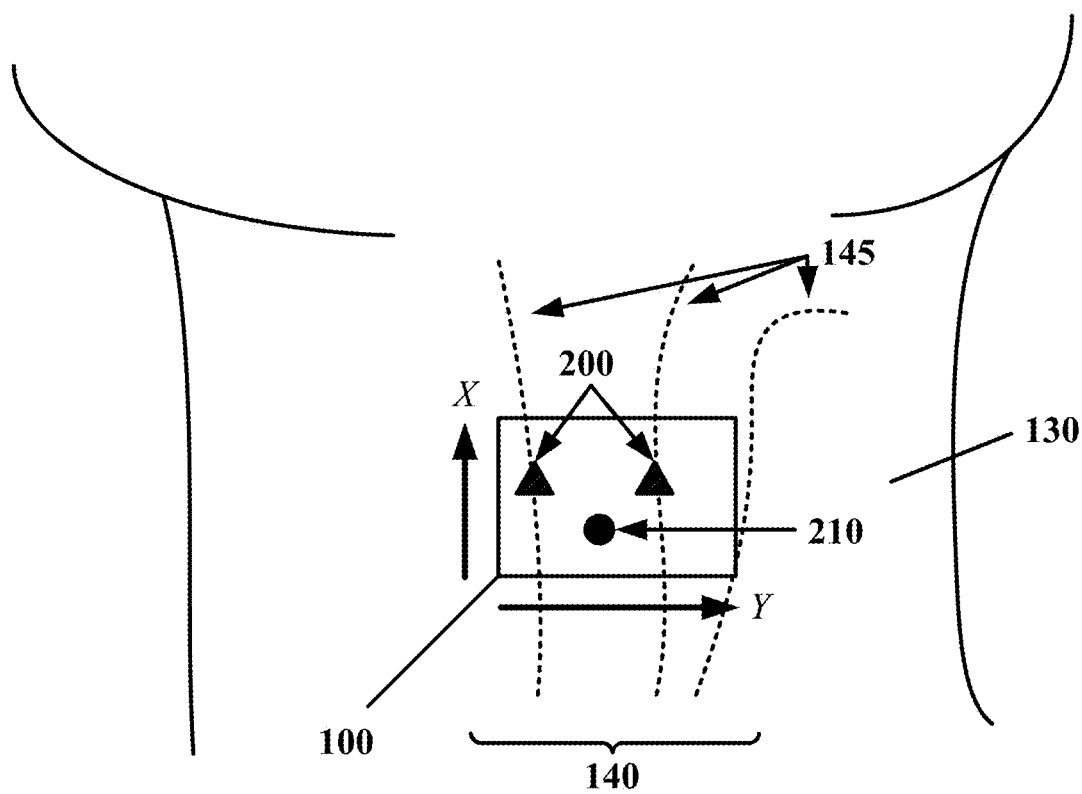
FIG. 2 is a schematic of a body part with an affixed stretchable electronic device.

FIG. 2 illustrates additional aspects of a stretchable electronic device 100 applied to the skin surface of a wrist 130 relative to features underlying the skin surface. The stretchable electronic device 100 applied to the skin surface of a wrist 130 in a position and orientation for best results of the stretchable electronic device 100. The wrist 130 includes a region of interest 140 which includes a plurality of blood vessels 145 under the skin. The stretchable electronic device 100 depicted in FIG. 2 has been applied so that the stretchable electronic device 100 is positioned and oriented to maximize operability of the stretchable electronic device 100. The stretchable electronic device 100 depicted in FIG. 2 has been applied so that the stretchable electronic device 100 is positioned and oriented to place two functional units 200 of the stretchable electronic device 100 on the surface of the wrist 130 at positions adjacent to underlying blood vessels 145. Depending on the embodiment, the two functional units 200 can be of one or more types that are the same as each other, or different from each other. The two functional units 200 of the stretchable electronic device 100 positioned on the skin surface adjacent to the underlying blood vessels 145 are of a type that operate more efficiently, and/or with better results, when positioned on a surface adjacent to an underlying blood vessel. For example, the functional units could include, in some embodiments, a pressure sensor configured to monitor blood pressure or pulse rate, and/or a light emitter and receiver configured for pulse oximetry. The stretchable electronic device 100 has been positioned and oriented relative to its major axes, identified as X and Y in FIG. 2. A third functional unit 210 of the stretchable electronic device 100 is not in a position adjacent to a blood vessel 145. The third functional unit can be of a type that does not operate more efficiently, and/or with better results, when positioned on a surface adjacent to an underlying blood vessel. For example, the third functional unit could include, depending on the embodiment, an antenna, a receiver, a transmitter, an energy harvesting device, or circuitry relating to another functional unit. In some embodiments, a stretchable electronic device can be positioned and oriented based on a combination of features of a body underlying the surface as well as those at the surface level (e.g. scars, wrinkles, pigmentation areas, neoplasias, etc.). In some embodiments, a stretchable electronic device includes a barrier layer that creates regions of higher and lower contact of functional units of the stretchable electronic device with an affixed surface. In some embodiments, a stretchable electronic device can be positioned and oriented on a surface of an object by a positional applicator device relative to the barrier layer of the stretchable electronic device, one or more functional units of the stretchable electronic device, and subsurface features of the object.

Figure 3:
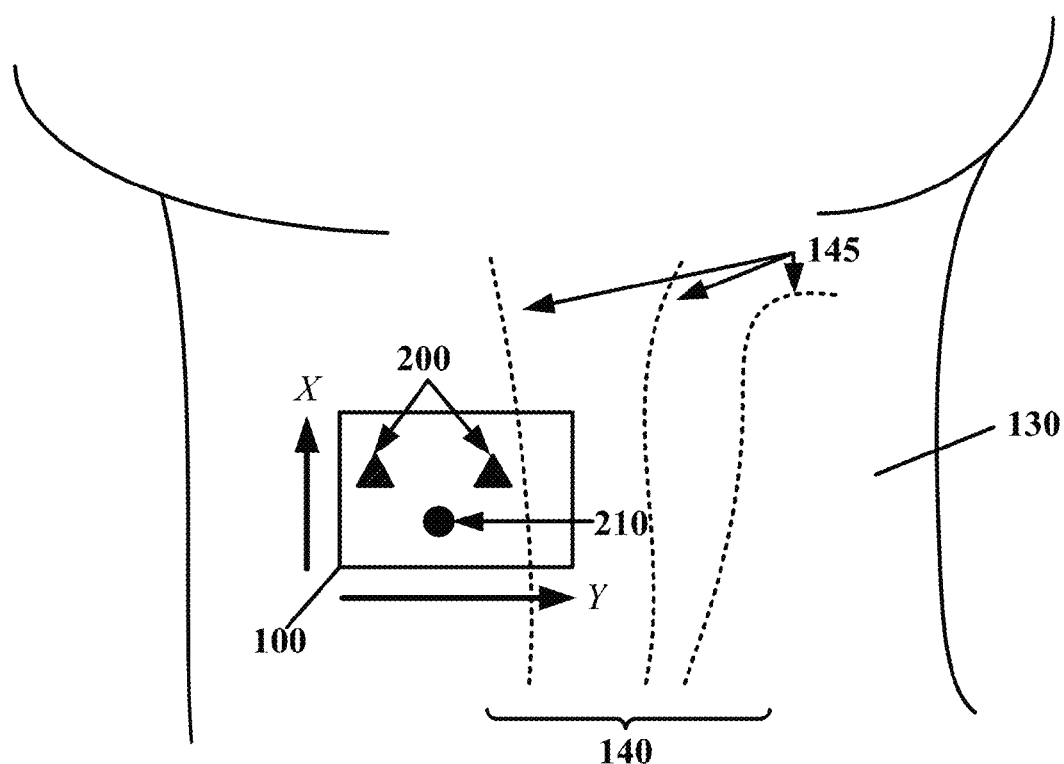
FIG. 3 is a schematic of a body part with an affixed stretchable electronic device.

FIG. 3 depicts aspects of a stretchable electronic device 100 applied to the skin surface of a wrist 130. The stretchable electronic device 100 depicted has not been applied to the skin surface of the wrist 130 in a position and orientation to maximize operability of the stretchable electronic device 100. The stretchable electronic device 100 depicted in FIG. 3 has been applied so that the stretchable electronic device 100 is positioned and oriented to place all of the functional units 200, 210 of the stretchable electronic device 100 on the surface of the wrist 130 at positions that are not adjacent to underlying blood vessels 145. The stretchable electronic device 100 has been positioned and oriented relative to its major axes, identified as X and Y in FIG. 3. Assuming that two of the functional units 200 of the stretchable electronic device 100 are of type that operate with maximum efficiency when they are placed on a skin surface adjacent to the blood vessels under the skin surface of the wrist, the position and orientation of the stretchable electronic device 100 shown in FIG. 3 does not promote maximum efficiency of the stretchable electronic device 100 for at least those functional units.

Figure 4:
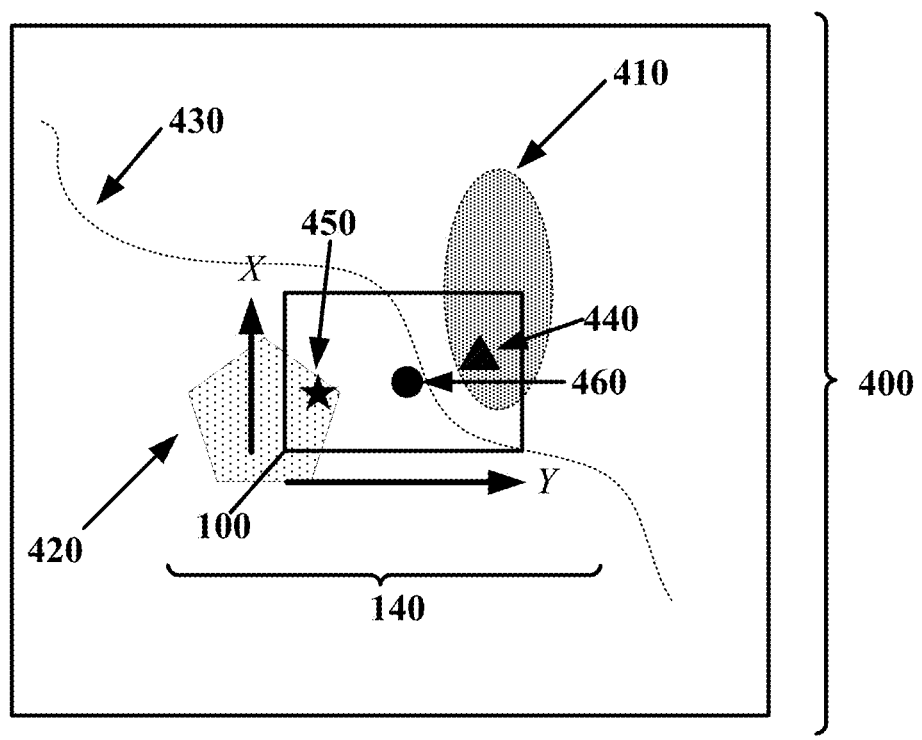
FIG. 4 is a schematic of an inanimate object with a stretchable electronic device affixed to the surface of a region of interest.

FIG. 4 depicts an inanimate object 400 with a stretchable electronic device 100 affixed to the surface of a region of interest 140 of the inanimate object 400. The stretchable electronic device 100 is oriented on the surface of the region of interest 140 of the inanimate object 400 relative to its major axes, identified as X and Y in FIG. 4. The region of interest 140 includes at least a first feature 410 and a second feature 420 underlying the surface. For example, depending on the embodiment, the features can include: a region that requires thermal monitoring, an electrical connection, a magnetic region, a motor, and/or a region of a structure that has the possibility of loosening or cracking due to stress or mechanical failure. Depending on the embodiment, a stretchable electronic device can include a plurality of functional units of the same or of different types. For example, depending on the embodiment, a stretchable electronic device can include a plurality of functional units including: temperature sensors, accelerometers, tension sensors, vibrations sensors, magnetic sensors, electrical sensors, antennas, transmitters, receivers, and associated circuitry. In some embodiments, a region of interest can also include structures at the surface that will influence the position and orientation of a stretchable electronic device, such as depressions, projections, connectors, edges, junctions, joints, seams, etc. The stretchable electronic device can also be positioned and oriented relative to these surface features as well as features underlying the surface.

The stretchable electronic device 100 depicted in FIG. 4 includes a first functional unit 440, a second functional unit 450, and a third functional unit 460. The stretchable electronic device 100 has been applied to the surface of the inanimate object 400 with an orientation and position so that the first functional unit 440 is positioned adjacent to the first feature 410. The stretchable electronic device 100 has been applied to the surface of the inanimate object 400 with an orientation and position so that the second functional unit 450 is positioned adjacent to the second feature 420. In addition, the stretchable electronic device 100 includes a third functional unit 460 that can detect an unknown sub-surface feature, such as a crack or fracture in the structure of the inanimate object 400. In the embodiment illustrated in FIG. 4, the third functional unit 460 may be able to detect an unknown sub-surface feature 430 that is a crack or fracture in the structure of the inanimate object 400 underlying the surface. An unknown sub-surface feature, such as a crack or fracture, may not be present initially in the structure of an inanimate object, but develop over time. A stretchable electronic device can, in some embodiments, be positioned and oriented so that one or more functional units of the stretchable electronic device are positioned adjacent to a subsurface region that has the potential for cracks and fractures, for example during stress or heat during use. A stretchable electronic device can, in some embodiments, be used to monitor for the potential of such subsurface features developing, changing, and/or expanding over time.

Figure 5:
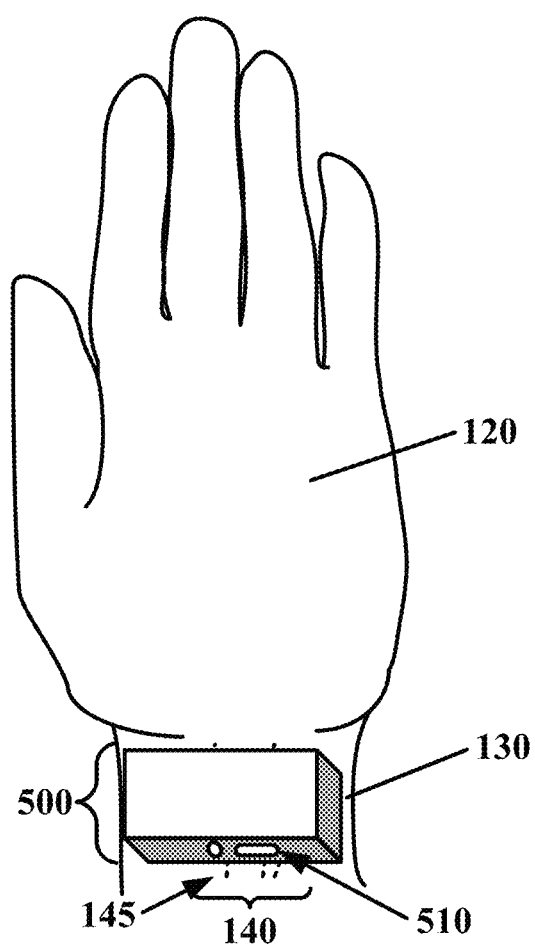
FIG. 5 is a schematic of a body part and a positional applicator device for a stretchable electronic device.

FIG. 5 depicts a human hand 120 with an associated wrist 130. The wrist 130 includes a region of interest 140. The region of interest 140 includes one or more features of interest, for example the illustrated blood vessels 145, under the surface of the skin. A positional applicator device 500 for applying a stretchable electronic device to a surface of an object, wherein the object is a part of a human body, is positioned on the wrist 130 surface adjacent to the region of interest 140. In some embodiments, the positional applicator device 500 includes a strap or other accessory to reversibly attach to the wrist during application of the stretchable electronic device to the surface. In some embodiments, the positional applicator device 500 includes at least one user interface 510. For example, a positional applicator device can include a user interface that is a display, one or more light indicators, one or more sound emitters, or other user interface structures.

In some embodiments, a positional applicator device for applying a stretchable electronic device to a surface of an object includes: a holder for a stretchable electronic device; a signal emitter positioned to direct an emitted signal toward a surface of an object; a receiver positioned to detect a return signal from the surface of the object; circuitry operably connected to the signal emitter and the receiver, the circuitry configured to compare the emitted signal with the return signal in order to identify surface and subsurface features of the object; circuitry configured to compare the identified surface and subsurface features with a map of surface and subsurface features of the object stored in memory; and a positioner operably affixed to the holder, the positioner positioned and structured to apply the stretchable electronic device to a position on the surface of the object based on the comparison. During use, a positional applicator device for applying a stretchable electronic device to a surface of an object is placed adjacent to a region of interest by a user, after which the positional applicator device seeks to detect one or more features of interest under the surface of the region of interest, and to apply at least one stretchable electronic device in a position and orientation relative to the one or more features of interest. In some embodiments, the positional applicator device seeks to detect one or more features of interest under the surface of the region of interest and on the surface of the region of interest, and to apply at least one stretchable electronic device in a position and orientation relative to the one or more features of interest in the subsurface and on the surface. In some embodiments, the positional applicator device includes memory including information regarding a previously generated representation of features under the surface of the region of interest, for example if the representation of features under the surface of the region of interest was previously generated during an earlier application of one or more stretchable electronic device(s).

As used herein, a 'map' can refer to location information regarding one or more surface and/or subsurface features of an object. For example, a map can include information regarding the relative spacing, absolute spacing, and/or location based on other features of an object. In some embodiments, a map can include one or more images. In some embodiments, a map can include distance information, such as distance between features or depth distance from the surface of the object. In some embodiments, a map can include directional information, such as directional information regarding the relative positions of two or more surface and/or subsurface features of the object.

In some embodiments, a positional applicator device for applying a stretchable electronic device to a surface of an object includes: a holder for a stretchable electronic device; a signal emitter positioned to direct an emitted signal toward a surface of an object; a signal receiver positioned to detect a return signal from the surface, the return signal originating with the emitted signal directed from the signal emitter; a controller including circuitry operably connected to the signal emitter and the signal receiver, the circuitry configured to compare the emitted signal with the return signal to form a representation of features of the object, and circuitry configured to compare the representation of features of the object with a representation of features of the stretchable electronic device; a user interface operably attached to the controller; a positioner operably affixed to the holder, the positioner positioned and structured to apply, in response to the controller, the stretchable electronic device to a position on the surface of the object based on the representation of features of the object and the representation of features of the stretchable electronic device; and an applicator of a size and shape to place the stretchable electronic device in contact with the surface of the object, the applicator including a switch operably attached to the controller. In some embodiments, the object is a body region. In some embodiments, the object is an inanimate object, such as a manufactured device or other object. In some embodiments, the object is part of a plant, for example a leaf, stem, or trunk.

Figure 6:
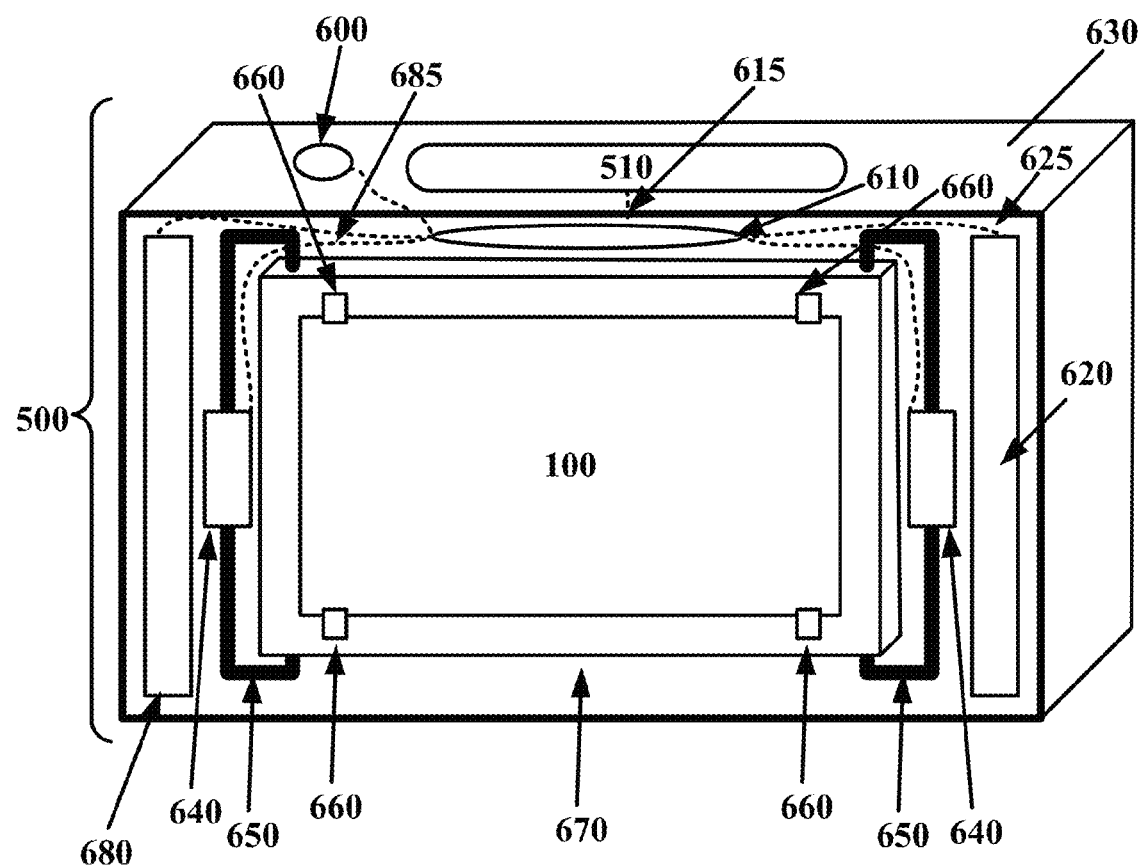
FIG. 6 is a schematic of a positional applicator device for a stretchable electronic device.

FIG. 6 illustrates aspects of an embodiment of a positional applicator device for applying a stretchable electronic device to a surface of an object. The positional applicator device 500 shown in FIG. 6 is shown with the side of the positional applicator device intended to be positioned adjacent to the surface of the object facing outward for purposes of illustration. The positional applicator device 500 includes a stretchable electronic device 100 reversibly affixed to the positional applicator device 500. The stretchable electronic device 100 is oriented so that the face of the stretchable electronic device 100 that will be in contact with the surface (e.g. of a wrist as in FIG. 5) is facing away from the device 500. Thus, when the positional applicator device 500 is placed on a surface (e.g. of a wrist as in FIG. 5), the face of the stretchable electronic device 100 that will be in contact with the surface is positioned adjacent to the surface. The positional applicator device 500 includes a shell 630 surrounding the sides of the positional applicator device 500 that are not facing the stretchable electronic device 100.

The stretchable electronic device is reversibly affixed to the positional applicator device by a holder for the stretchable electronic device. In the embodiment shown in FIG. 6, a stretchable electronic device 100 is affixed to the holder 670 with reversible fasteners 660. In some embodiments, the holder includes a reversible fastener for the stretchable electronic device, the fastener positioned to stabilize the stretchable electronic device. In some embodiments, the holder includes a frame configured to surround one or more edges of the stretchable electronic device. The frame can include, for example, one or more reversible fasteners for the stretchable electronic device. In some embodiments, the holder includes a reel of a size and shape to hold at least one stretchable electronic device, a motor operably attached to the reel. For example, in some embodiments a plurality of stretchable electronic devices can be affixed to a flexible backing sheet, and curled into a roll which is affixed to the reel. The motor attached to the reel can advance the flexible backing sheet as needed to bring forward one or more stretchable electronic devices in the roll.

In some embodiments, the holder includes a manipulator positioned to alter the size of the stretchable electronic device. For example, a manipulator can include a cutting implement for the stretchable electronic device. For example, a manipulator can include a cutting implement oriented to trim any unwanted excess material, such as excess backing sheet, from a stretchable electronic device before or after application of the stretchable electronic device to the surface. For example, a manipulator can include a cutting implement oriented to alter the size or shape of the stretchable electronic device, such as rounding corners or trimming edges of the stretchable electronic device in order to better align the stretchable electronic device with the surface. In some embodiments, the controller sends operational signals to the manipulator in response to the representation of features of the object and the representation of features of the stretchable electronic device. In some embodiments, the manipulator is under the control of the controller, and the stretchable electronic device is trimmed in reference to information in the controller. For example, a controller may send signals to the cutting implement to trim the stretchable electronic device in response to information about the surface of the object, for example the topography of the region. For example, a controller may send signals to the cutting implement to trim the stretchable electronic device in response to information about a feature on a surface of an object that is an inanimate object, such as a bracket, holder, crack, or joint. For example, a controller may send signals to the cutting implement to trim the stretchable electronic device in response to information about a feature on a surface of an object that is a body, such as a scar.

In some embodiments, the holder includes an adaptable tensioner of a size, shape and position to control tension of the stretchable electronic device. For example, an adaptable tensioner can control tension of the stretchable electronic device along one or more major axes of the stretchable electronic device (e.g. axes X and Y in FIGS. 2, 3 and 4). In some embodiments, the holder is operably connected to the controller, and configured to detect the stretchable electronic device in response to a signal originating with the controller. In some embodiments, a positional applicator device includes a storage region of a size and shape to retain a plurality of stretchable electronic devices, the storage region operably attached to the holder.

In the embodiment illustrated in FIG. 6, the stretchable electronic device 100 is reversibly affixed to the positional applicator device 500 by a holder that includes a set of reversible fasteners 660. For example, the reversible fasteners can include clips or restraining tabs, depending on the embodiment. Although the embodiment illustrated in FIG. 6 includes a set of reversible fasteners 660 that are four fasteners, in some embodiments there may be more or less than four reversible fasteners. Some embodiments include one reversible fastener. Some embodiments include two reversible fasteners. Some embodiments include three reversible fasteners. Some embodiments include five reversible fasteners. Some embodiments include six reversible fasteners. Some embodiments include more than six reversible fasteners. The reversible fasteners 660 shown in FIG. 6 are positioned near the ends of the long axes of the edges of the stretchable electronic device 100. The number, position and spacing of the reversible fasteners can vary depending on the embodiment. Some embodiments include a variable number of reversible fasteners oriented and positioned for use with different embodiments of a stretchable electronic device.

In an embodiment, a stretchable electronic device includes a signal emitter positioned and adapted to direct an emitted signal toward a surface of an object. In some embodiments, the signal emitter is an optical signal emitter. For example, the signal emitter can be a light source. For example, the signal emitter can be a light source that includes an LED and/or a laser. In some embodiments, the signal emitter is a near-IR signal emitter. In some embodiments, the signal emitter is an ultrasound emitter. In some embodiments, the signal emitter is a radio frequency (RF) emitter. In some embodiments, the signal emitter is operably connected to the controller, for example with a wired or wireless connector. In some embodiments, the signal emitter includes sub-emitters of the same type, for example a signal emitter can include two or more light sources. For example, a signal emitter can include two or more sub-emitters, each of the sub-emitters including at least one LED. In some embodiments, the signal emitter includes sub-emitters of different types, for example a signal emitter can include a light source and an RF emitter. In some embodiments, the signal emitter is positioned at a predetermined distance from the surface of the object. In some embodiments, the signal emitter is positioned to be in contact with the surface of the object.

In the embodiment depicted in FIG. 6, the positional applicator device 500 includes a signal emitter 620 positioned adjacent to an edge of the positional applicator device 500. In some embodiments, the signal emitter is an optical signal emitter. For example, the signal emitter can be a light source. For example, the signal emitter can be a light source that includes an LED and/or a laser. In some embodiments, the signal emitter is an ultrasound emitter. In some embodiments, the signal emitter is a radio frequency (RF) emitter. In some embodiments, the signal emitter is operably connected to the controller, for example with a wired or wireless connector. In some embodiments, the signal emitter includes sub-emitters of the same type, for example a signal emitter can include two or more light sources. For example, a signal emitter can include two or more sub-emitters, each of the sub-emitters including at least one LED. In some embodiments, the signal emitter includes sub-emitters of different types, for example a signal emitter can include a light source and an RF emitter. In the depicted embodiment, the signal emitter 620 is connected to the controller 610 with a wire connector 625. Depending on the embodiment, the controller can include circuitry and/or programming configured to send control signals to the signal emitter to turn on and off. For example, in some embodiments, the signal emitter can receive control signals from the controller to operate with a single pulse, and in some embodiments the signal emitter can receive signals from the controller to operate with multiple pulses. The signal emitter can be positioned and oriented to direct a signal at one or more predetermined angle(s) relative to the surface of the object. For example, a signal emitter can be positioned and oriented to direct a signal at a predetermined angle relative to the surface of the object, the angle predicted to result in a maximum level of signal reflected from the surface to the signal receiver of the positional applicator device. For example, a signal emitter can be positioned and oriented to direct a signal at a series of predetermined angles relative to the surface of the object in multiple bursts of signal, the angles predicted to result in a maximum level of total signal reflected from the surface to the signal receiver of the positional applicator device. The signal emitter can be of a type configured to emit one or more signals of predetermined duration and intensity. The signal emitter can be of a type configured to emit a series of signals in a predetermined pattern.

In an embodiment, a positional applicator device includes a signal receiver positioned and adapted to detect a return signal from the surface, the return signal originating with the emitted signal directed from the signal emitter. In some embodiments, a positional applicator device includes a signal receiver oriented to detect a return signal from the surface. In some embodiments, a positional applicator device includes a signal receiver of a type to detect an emitted signal originating from the signal emitter and reflected from the surface of the object. For example, if the positional applicator device includes a signal emitter that is a light source, the positional applicator device includes an optical signal receiver that can detect a return signal from the emitted light that is reflected from the object. In some embodiments, a positional applicator device includes an optical signal receiver. In some embodiments, a positional applicator device includes an ultrasound receiver. In some embodiments, a positional applicator device includes an RF receiver.

The embodiment depicted in FIG. 6 includes a positional applicator device 500 including a signal receiver 680. The positional applicator device 500 includes a signal receiver 680 positioned adjacent to an edge of the device 500. In the depicted embodiment, the signal receiver 680 is connected to the controller 610 with a wire connector 685. Depending on the embodiment, the controller can include circuitry and/or programming configured to receive signals from the signal receiver, for example signals including information regarding received signals. Depending on the embodiment, the controller can include circuitry and/or programming configured to send signals to the signal receiver, for example to turn on and off. The signal receiver can be positioned and oriented to detect a signal at one or more predetermined angle(s) relative to the surface of the object. For example, a signal receiver can be positioned and oriented to detect a signal at a predetermined angle relative to the surface of the object, the angle predicted to result in a maximum level of signal emitted from the signal emitter and reflected from the surface to the signal receiver of the positional applicator device. For example, a signal receiver can be positioned and oriented to detect a signal emitted at a series of predetermined angles relative to the surface of the object in multiple bursts of signal, the angles predicted to result in a maximum level of total signal reflected from the surface to the signal receiver of the positional applicator device. The signal receiver can be of a type configured to detect one or more signals of predetermined duration and intensity. The signal receiver can be of a type configured to detect a series of signals in a predetermined pattern. The signal receiver can be of a type configured to detect a series of signals in a predetermined series and/or frequency.

A positional applicator device includes a controller including circuitry operably connected to the signal emitter and to the signal receiver, the circuitry configured to compare the emitted signal with the return signal to form a representation of features of the object, and circuitry configured to compare the representation of features of the object with a representation of features of the stretchable electronic device. In some embodiments, a controller includes electronic memory including information regarding features of the stretchable electronic device. For example, a controller can include electronic firmware memory including features of one or more standard models of stretchable electronic devices. For example, a controller can include in electronic memory a look-up table including features of one or more standard models of stretchable electronic devices. For example, a controller can include electronic software memory including features of one or more standard models of stretchable electronic devices. In some embodiments, a controller includes electronic memory including information regarding features of the stretchable electronic device that are accepted from a user interface. For example, a controller can include in memory a model number or identification code accepted from a user interface. In some embodiments, a controller includes electronic memory including information regarding features of the stretchable electronic device that were generated by the positional applicator device, for example with use of an optical scanner. In some embodiments, the electronic memory including information regarding features of the stretchable electronic device includes information regarding a feature of the stretchable electronic device that includes a sensor. In some embodiments, the electronic memory including information regarding features of the stretchable electronic device includes information regarding a feature of the stretchable electronic device that includes a transcutaneous drug delivery device. In some embodiments, the electronic memory including information regarding features of the stretchable electronic device includes information regarding a feature of the stretchable electronic device that includes a nerve stimulator. In some embodiments, the electronic memory including information regarding features of the stretchable electronic device includes information regarding a feature of the stretchable electronic device that includes an antenna. In some embodiments, the electronic memory including information regarding features of the stretchable electronic device includes information regarding a feature of the stretchable electronic device that includes a thermocouple.

In some embodiments, a controller includes electronic memory including information regarding features of the object. In some embodiments, the object is a body. For example, in some embodiments electronic memory including information regarding features of the object that is a body includes information regarding at least one epidermal structure. When the object is a body, the information regarding at least one epidermal structure can include features such as scars, wrinkles or epidermal pigmentation. For example, in some embodiments electronic memory including information regarding features of the object includes information regarding at least one subcutaneous structure of a body. For example, the information regarding at least one subcutaneous structure of a body can include bone position and composition, the placement and structure of any implanted devices in the body, the placement and structure of a subcutaneous neoplasia, and/or the placement and structure of subcutaneous scar tissue. For example, in some embodiments electronic memory including information regarding features of the object that is a body includes information regarding at least one edge structure of the body. For example, in some embodiments electronic memory including information regarding features of the object that is a body includes information as to the curvature, size, position and/or relative positioning of a body part. For example, in some embodiments electronic memory including information regarding features of the object that is a body includes electronic memory including information regarding at least one prior stretchable electronic device that was previously affixed to the surface of the body.

In some embodiments, the object is an inanimate object. In some embodiments, a controller includes electronic memory including information regarding features of the inanimate object. In some embodiments, a controller includes electronic memory including information regarding features of the object including at least one edge structure of the object. For example, in some embodiments electronic memory including information regarding features of the object that is an inanimate object includes information as to the curvature, size, position and/or relative positioning of one or more sections and edge regions of the inanimate object. In some embodiments, a controller includes electronic memory including information regarding features of the inanimate object including electronic memory including information regarding at least one prior stretchable electronic device that was previously affixed to the surface of the inanimate object.

A positional applicator can include a user interface operably attached to the controller. A user interface can include, for example, a display. A user interface can include, for example, a light emitter such as an indicator light. A user interface can include, for example, a sound emitter. A user interface can include, for example, a buzzer. A user interface can include, for example, a touchscreen. A user interface can include, for example, an on/off switch.

The embodiment of a positional applicator device 500 illustrated in FIG. 6 includes a user interface 510 that is a display. The display is operably attached to the controller 610 with a wire connector 615. The display can be configured to activate in response to signals sent by the controller 610 through the wire connector 615. The illustrated embodiment also includes a user interface 600 that is an indicator light operably connected to the controller 615 with a wire connector.

A positional applicator device includes a positioner operably affixed to the holder, the positioner positioned and structured to apply, in response to the controller, the stretchable electronic device to a position on the surface of the object relative to the representation of features of the object and the representation of features of the stretchable electronic device. In some embodiments, the positioner includes at least one fastener affixed to the holder, and a motor attached to the fastener, the motor operably attached to the controller. In some embodiments, the motor is positioned to allow adjustment of position of the stretchable electronic device relative to the surface of the inanimate object. For example, the motor can be oriented and configured to move the entire stretchable electronic device relative to the surface of the inanimate object. In some embodiments, the motor is positioned to allow adjustment of orientation of the stretchable electronic device relative to the surface. For example, the motor can be oriented and configured to alter the orientation of the entire stretchable electronic device relative to the surface.

In the embodiment illustrated in FIG. 6, the positional applicator device 500 includes a positioner operably affixed to the holder 670. The positioner includes fasteners 650 affixed to each end of the holder 670. The illustrated embodiment includes two fasteners 650, one affixed to either end of the holder 670. The positioner illustrated includes a motor 640 affixed to each of the fasteners 650. Each of the motors 640 are connected to the controller 610 with a wire connector. The positioner, including the two fasteners 650, each affixed to an end of the holder 670, and the motors 640 are positioned and structured to apply, in response to signals received from the controller 610, the stretchable electronic device 100 to a position on a surface of an object. Depending on the embodiment, the positioner can move the stretchable electronic device along one or more X and/or Y axes (e.g. left/right and up/down in the illustration of FIG. 6). In some embodiments, the positioner can rotate the stretchable electronic device relative to the X and Y axes.

A positional applicator device includes an applicator of a size and shape to place the stretchable electronic device in contact with the surface of the object, the applicator including a switch operably attached to the controller. In some embodiments, an applicator includes an adaptable tensioner of a size, shape and position to control tension of the stretchable electronic device during application. For example, an adaptable tensioner can control the tension and/or stretch of a stretchable electronic device prior to application to a surface. For example, an adaptable tensioner can control the tension and/or stretch along one or more axes of the stretchable electronic device.

In some embodiments, a positional applicator device includes a sprayer positioned to apply material to the surface of the object, and a reservoir operably attached to the sprayer. In some embodiments, the sprayer includes a switch responsive to the controller. For example, a reservoir can include compressed gas, and the sprayer can be used to dry the surface of the object prior to application of the stretchable electronic device. For example, a reservoir can include a liquid adhesive, and the sprayer can be used to apply a coating of the adhesive to a region of the surface of the object prior to application of the stretchable electronic device to the same region of the surface. In some embodiments, the reservoir includes an adhesive formulated to adhere a surface of the stretchable electronic device to the surface of the object. The positional applicator device can, for example, administer the adhesive to the surface of the object prior to placement of the stretchable electronic device on the surface. The positional applicator device can, for example, administer the adhesive to the surface of the object after placement of the stretchable electronic device on the surface.

In some embodiments, a positional applicator device includes a gas blower positioned to direct gas to the surface of the object, a switch affixed to the gas blower, the switch responsive to the controller. For example, a gas blower can be configured and positioned to direct ambient air against the surface of the object prior to application of the stretchable electronic device.

In some embodiments, a positional applicator device includes an abrader of a size and shape to remove a portion of the surface of the object, a holder affixed to the abrader, and a positioner affixed to the abrader, the positioner oriented to position the abrader relative to the surface of the object. For example, the abrader can be positioned and configured to remove adhesive, prior stretchable electronic device components, dirt and/or debris from the surface of the object. In embodiments wherein the stretchable electronic device is applied to an object that is a body, the abrader can be configured to remove a quantity of superficial skin. In embodiments wherein the stretchable electronic device is applied to an object that is a body, the abrader can be configured to remove a quantity of cosmetics from the surface of the skin prior to application of the stretchable electronic device to the surface.

In some embodiments, a positional applicator device includes one or more projections positioned and oriented to contact the surface of the object and one or more adaptable tensioners affixed to the one or more projections and responsive to the tension of the surface. For example, the projections can be positioned and oriented to maintain the position of the positional applicator device relative to the surface of the object prior to action of the one or more adaptable tensioners and application of a stretchable electronic device to the surface. In some embodiments, a positional applicator device includes an indicator that is configured to send a signal to a user when the projections are in contact with the surface. In some embodiments, a positional applicator device includes an indicator that is configured to send a signal to a user when the projections are in contact with the surface but the region of interest is not in an appropriate position relative to the positional applicator device. For example, the indicator can include an auditory indicator with pre-recorded messages such as "move the device a centimeter to the left." For example, the indicator can include an auditory indicator with pre-recorded messages such as "rotate the device a half-turn clockwise."

In some embodiments, a positional applicator device includes a light source positioned to direct light in a visible pattern toward the surface of the object. For example, a visible pattern may indicate to a user where to place and hold the positional applicator device relative to the surface of the object for application of the stretchable electronic device to the surface. Some embodiments include a switch operably attached to the light source, the switch operably attached to the controller. For example, the controller can include circuitry configured to turn on the light source and then to send a signal to initiate a particular display as needed for a particular situation in order to assist a user to position the positional applicator device appropriately for application of a particular stretchable electronic device to a region of the surface. A light display can, for example, be of a type to indicate the exact position of the positional applicator device appropriately for application of a particular stretchable electronic device to a region of the surface. A light display can, for example, be of a type to show a user how to move the positional applicator device relative to a region of the surface appropriately for application of a particular stretchable electronic device.

In some embodiments, a positional applicator device includes an auditory signal emitter operably attached to the controller. In some embodiments, a positional applicator device includes a user interface operably attached to the controller. In some embodiments, a positional applicator device includes a shell positioned adjacent to at least one side of the positional applicator device, the shell forming at least one external wall of the positional applicator device. In the embodiment shown in FIG. 6, the positional applicator device 500 includes a shell 630 that surrounds 5 sides of the device, with the side positioned forward in the illustration configured as an aperture in the shell 630. For example, a shell can include one or more thin walls. For example, a shell can be fabricated from a rigid plastic or metal material, or a composite material. In some embodiments, a positional applicator device includes a handle attached to the positional applicator device, the handle of a size, shape and orientation to assist a user to orient the positional applicator device relative to the surface of the object. For example, a positional applicator device can include a shell, and a handle affixed to the shell. In some embodiments, a positional applicator device includes an accelerometer, the accelerometer operably attached to the controller. For example, a controller can be configured to accept information from an accelerometer regarding motion of the positional applicator device, and for the controller to only initiate application of the stretchable electronic device to a region of the surface when the positional applicator device is stable and/or not moving.

In some embodiments, a positional applicator device for applying a stretchable electronic device to a surface of an object includes: a holder for a stretchable electronic device; a signal emitter positioned to direct an emitted signal toward a surface of an object; a signal receiver positioned to detect a return signal from the surface, the return signal originating with the emitted signal directed from the signal emitter; a controller including circuitry operably connected to the signal emitter and the signal receiver, the circuitry configured to compare the signal with the return signal to form a representation of features of the object, and circuitry configured to compare the representation of features of the object with a representation of features of the stretchable electronic device; a positioner operably affixed to the holder, the positioner positioned and structured to apply, in response to the controller, the stretchable electronic device to a position on the surface of the object based on the representation of features of the object and the representation of features of the stretchable electronic device; a stabilizer of a size and shape to stabilize the surface of the object relative to the positioner; and an applicator of a size and shape to place the stretchable electronic device in contact with the surface of the object, the applicator including a switch operably attached to the controller. In some embodiments, the stabilizer includes a structure including a surface of a size and shape for reversibly mating with a surface of the object. In some embodiments, the stabilizer includes a fastener of a size and shape to affix the object to the positional applicator device.

Figure 7:
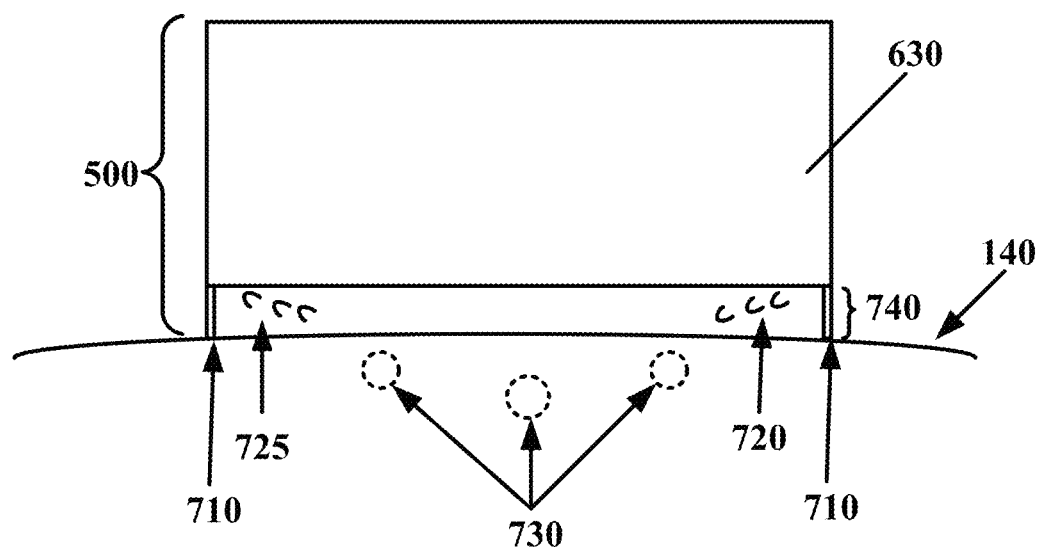
FIG. 7 is a schematic of a positional applicator device for a stretchable electronic device in position relative to a surface of an object.

FIG. 7 illustrates a positional applicator device 500 positioned relative to a region of interest 140 of an object. FIG. 7 depicts the positional applicator device 500 and the region of interest 140 in cross-section for purposes of illustration. The positional applicator device 500 includes stabilizers 710. In the embodiment illustrated, the stabilizers are positioned at the edges of a shell 630 of the positional applicator device 500. The stabilizers 710 are positioned and oriented to contact the surface of the object. Each of the stabilizers 710 includes a structure including a surface of a size and shape for reversibly mating with a surface of the object. Each of the illustrated stabilizers 710 illustrated is substantially linear, and has a proximal end affixed to the shell 630 of the positional applicator device 500 and a distal end in contact with the surface of the region of interest 140. The stabilizers 710 are of a size and shape to position the positional applicator device 500 at a fixed distance 740 from the surface of the region of interest 140.

Prior to application of a stretchable electronic device to the surface of a region of interest 140, the positional applicator device sends signals 720 from one or more signal emitters and receives signals 725 reflected from the surface. In embodiments including stabilizers 710, there can be a fixed distance 740 between the signal emitter(s), the signal receiver(s) and the surface. The signals 720, 725 are of a type to detect subsurface features 730 under the surface of the region of interest 140. In embodiments where the object is a body, for example, the signals may be of a type to detect subsurface nerves, blood vessels, implanted structures and/or musculature. In embodiments where the object is an inanimate object, for example, the signals may be of a type to detect subsurface cracks, impurities, flaws, layers of composite materials, wires, fiberoptic cables and/or components. In embodiments where the object is an inanimate object, for example, the signals may be of a type to detect subsurface motion and/or heat generated from a subsurface feature such as a motor or a fan.

Figure 8:
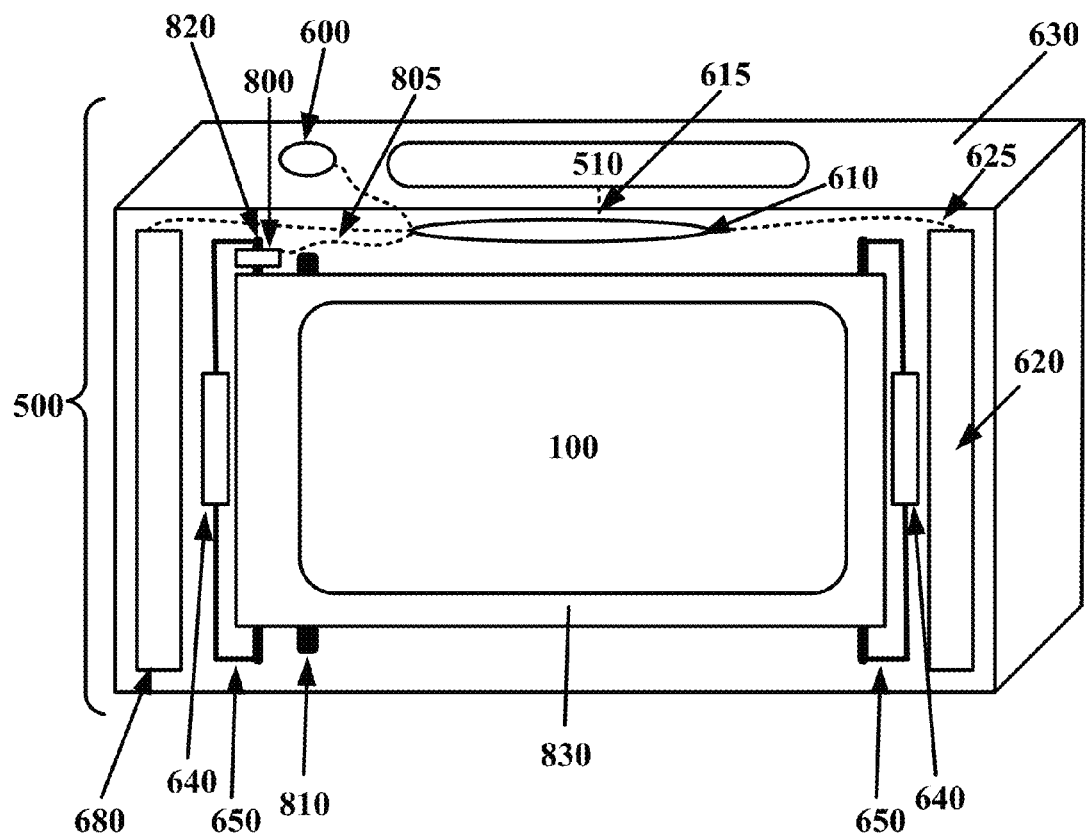
FIG. 8 is a schematic of a positional applicator device for a stretchable electronic device.

FIG. 8 illustrates aspects of an embodiment of a positional applicator device 500. The positional applicator device 500 includes a stretchable electronic device 100 that includes a holder that includes a flexible sheet 830. A stretchable electronic device 100 is affixed to the flexible sheet 830 with a reversible adhesive on the face of the stretchable electronic device 100 against the flexible sheet 830, which is the reverse face of the stretchable electronic device 100 from that which will be positioned adjacent to the surface of the object. The holder includes a reel 820 around which the flexible sheet 830 is wound. In some embodiments, there are a plurality of stretchable electronic devices reversibly affixed to the surface of the flexible sheet, some of the plurality of stretchable electronic devices being wound around the reel with one or more sections of the flexible sheet. A motor 800 is affixed to the reel 820. The motor 800 is operably attached to the controller 610 with a wire connector 805. The motor 800 rotates the reel 820 in response to signals sent by the controller 610. In the embodiment illustrated, the fastener 650 of the positioner is affixed to the reel 820, and a motor 640 is attached to the fastener 650.

The embodiment of a positional applicator device 500 illustrated in FIG. 8 includes an adaptable tensioner 810. The adaptable tensioner 810 is of a size, shape and position to control tension of the stretchable electronic device 100 during application to the surface. The adaptable tensioner 810 illustrated in FIG. 8 is a rod positioned adjacent to the face of the flexible sheet 830 opposite to the face of the flexible sheet 830 reversibly attached to the stretchable electronic device 100. A positioner is affixed to the rod behind the flexible sheet 830, the positioner of a type to alter the pressure that the rod places on the flexible sheet 830 and the stretchable electronic device 100 affixed to the flexible sheet 830.

In some embodiments, a positional applicator device for applying a stretchable electronic device to a surface of an object includes: a holder for a stretchable electronic device; a receiver positioned to detect a return signal from a surface of an object; circuitry operably connected to the receiver, the circuitry configured to identify surface and subsurface features of the object based on the return signal; and a positioner operably affixed to the holder, the positioner positioned and structured to apply the stretchable electronic device to a position on the surface of the object relative to the comparison. In some embodiments, the object is a body. In some embodiments, the object is an inanimate object. In some embodiments, the object is a plant.

In some embodiments, the receiver is a light receiver. For example, the light receiver can be a camera, such as a digital camera. The light receiver can be of a type that is operational in the visible spectrum. The light receiver can be of a type that is operational in the near-visible spectrum, such as IR, near-IR, or ultraviolet.

In some embodiments, the receiver is an auditory signal receiver. For example, the receiver can be of a type to accept auditory signals from the object, and to process the received signals into information which is then transmitted to the attached circuitry.

In some embodiments, a positional applicator device for applying a stretchable electronic device to a surface of an object includes: circuitry including memory; and circuitry configured to compare the identified features with subsurface features of the object stored in the memory. For example, the memory can be digital memory. For example, the memory can be electronic memory. For example, the memory can include a look-up table including information regarding specific sounds, such as those that indicate a specific subsurface feature, such as a motor or fan in an inanimate object, or a pulse in a body, or a respiration site in a plant.

In some embodiments, a method of applying a stretchable electronic device to a surface of an object includes: initiating a signal from a signal emitter, the emitted signal directed to a surface of an object; detecting, with a receiver, a return signal from the emitted signal; comparing, with circuitry, the emitted signal and the received return signal; forming a representation of features of the object based on the comparison; and positioning a stretchable electronic device relative to the surface of the object in relation to the map. In some embodiments, the method also includes applying the stretchable electronic device to the surface of the object.

FIG. 9 illustrates aspects of a method of applying a stretchable electronic device to a surface of an object. Box 900 shows that the method is a method of applying a stretchable electronic device to a surface of an object. Box 910 depicts initiating a signal from a signal emitter, the signal directed to a surface of an object. Box 920 shows detecting, with a receiver, a return signal from the emitted signal. Box 930 illustrates comparing, with circuitry, the initiated signal and the received return signal. Box 940 shows forming a representation of features of the object based on the comparison. Box 950 depicts positioning a stretchable electronic device relative to the surface of the object in relation to the map. Optional box 960 illustrates applying the stretchable electronic device to the surface of the object.

In some embodiments, a method of applying a stretchable electronic device to a surface of an object includes: retaining a stretchable electronic device with a holder of a device; initiating an emitted signal from a signal emitter of the device, the emitted signal directed to a surface of an object; detecting, with a signal receiver of the device, a return signal from the emitted signal; comparing, with circuitry of the device, the emitted signal and the received return signal; forming, in circuitry of the device, a representation of features of the object based on the comparison; comparing, in circuitry of the device, a representation of features of the stretchable electronic device with the formed representation of features of the object based on the comparison; indicating, with a user interface of the device, a position for the stretchable electronic device relative to the surface of the object; and applying the stretchable electronic device to the surface of the object.

In some embodiments, a method of applying a stretchable electronic device to a surface of an object includes initiating an emitted signal from a signal emitter of the device, the emitted signal directed to a surface of an object, and the initiating an emitted signal includes initiating an optical signal directed to the surface of the object. In some embodiments, a method of applying a stretchable electronic device to a surface of an object includes initiating an emitted signal from a signal emitter of the device, the emitted signal directed to a surface of an object, and the initiating a emitted signal includes initiating an ultrasound signal directed to the surface of the object. In some embodiments, a method of applying a stretchable electronic device to a surface of an object includes initiating an emitted signal from a signal emitter of the device, the emitted signal directed to a surface of an object, and the initiating an emitted signal includes initiating a RF signal directed to the surface of the object. In some embodiments, a method of applying a stretchable electronic device to a surface of an object includes initiating an emitted signal from a signal emitter of the device, the emitted signal directed to a surface of an object, and the initiating an emitted signal includes initiating an emitted signal from a signal emitter at a time to create a return signal from the surface of the object wherein the return signal is positioned to be received by the signal receiver of the device. In some embodiments, the signal from the signal emitter can be emitted with an energy calculated relative to one or more of: the distance between the signal emitter and the surface, the orientation of the signal emitter to the surface, the composition of the expected subsurface features of the object, and/or the composition of the surface.

In some embodiments, a method of applying a stretchable electronic device to a surface of an object includes detecting, with a signal receiver of the device, a return signal from the emitted signal and the detecting, with a signal receiver of the device, a return signal from the emitted signal includes detecting an optical signal directed from the surface of the object. In some embodiments, a method of applying a stretchable electronic device to a surface of an object includes detecting, with a signal receiver of the device, a return signal from the emitted signal and the detecting, with a signal receiver of the device, a return signal from the emitted signal includes detecting an ultrasound signal directed from the surface of the object. In some embodiments, a method of applying a stretchable electronic device to a surface of an object includes detecting, with a signal receiver of the device, a return signal from the emitted signal and the detecting, with a signal receiver of the device, a return signal from the emitted signal includes detecting an RF signal directed from the surface of the object.

In some embodiments, a method of applying a stretchable electronic device to a surface of an object includes comparing, with circuitry of the device, the initiated signal and the received return signal, and the comparing includes: forming, in circuitry of the device, a representation of features of the object; and comparing, in circuitry of the device, the representation of features of the object with a representation of features of the stretchable electronic device. For example, the method can include accessing a look-up table in memory with positions and orientations of features of the stretchable electronic device to be aligned with subsurface features of the object. For example, the method can include accessing a look-up table in memory with apertures in a barrier layer covering all or part of the stretchable electronic device to be aligned with subsurface features of the object.

In some embodiments, a method of applying a stretchable electronic device to a surface of an object includes forming, in circuitry of the device, a representation of features of the object based on the comparison, and the forming includes providing, from electronic memory of the device, information regarding features of the object. For example, the providing, from electronic memory of the device, information regarding features of the object can include information regarding at least one epidermal structure of the object. For example, the providing, from electronic memory of the device, information regarding features of the object can include information regarding at least one subcutaneous structure of a body. For example, the providing, from electronic memory of the device, information regarding features of the object can include information regarding at least one edge structure of the object. In some embodiments, a method of applying a stretchable electronic device to a surface of an object includes forming, in circuitry of the device, a representation of features of the object based on the comparison, and the forming includes providing, from electronic memory of the device, information regarding at least one prior stretchable electronic device that was previously affixed to the surface.

In some embodiments, a method of applying a stretchable electronic device to a surface of an object includes comparing, in circuitry of the device, a representation of features of the stretchable electronic device with the formed representation of features of the object based on the comparison includes providing, from electronic memory of the device, information regarding features of the stretchable electronic device. For example, in some embodiments, the providing, from electronic memory of the device, information regarding features of the stretchable electronic device includes providing information regarding a feature of the stretchable electronic device that includes a sensor. For example, in some embodiments, the providing, from electronic memory of the device, information regarding features of the stretchable electronic device includes providing information regarding a feature of the stretchable electronic device that includes a transcutaneous drug delivery device. For example, in some embodiments, the providing, from electronic memory of the device, information regarding features of the stretchable electronic device includes providing information regarding a feature of the stretchable electronic device that includes a nerve stimulator. For example, in some embodiments, the providing, from electronic memory of the device, information regarding features of the stretchable electronic device includes providing information regarding a feature of the stretchable electronic device that includes an antenna. For example, in some embodiments, the providing, from electronic memory of the device, information regarding features of the stretchable electronic device includes providing information regarding a feature of the stretchable electronic device that includes a thermocouple. For example, in some embodiments, the providing, from electronic memory of the device, information regarding features of the stretchable electronic device includes the special orientation and/or relative positioning of multiple features of the stretchable electronic device.

In some embodiments, a method of applying a stretchable electronic device to a surface of an object includes indicating, with a user interface of the device, a position for the stretchable electronic device relative to the surface of the object. In some embodiments, indicating a position includes indicating that the user should stop moving the stretchable electronic device relative to the surface of the object. In some embodiments, indicating a position includes indicating a direction or amount that the user should move or rotate the stretchable electronic device relative to the surface of the object. In some embodiments, a method of applying a stretchable electronic device to a surface of an object includes indicating, with a user interface of the device, a position for the stretchable electronic device relative to the surface of the object, and the indicating includes indicating on a visual representation of the user interface. In some embodiments, a method of applying a stretchable electronic device to a surface of an object includes indicating, with a user interface of the device, a position for the stretchable electronic device relative to the surface of the object, and the indicating includes initiating a signal from a sound emitter. In some embodiments, a method of applying a stretchable electronic device to a surface of an object includes indicating, with a user interface of the device, a position for the stretchable electronic device relative to the surface of the object, and the indicating includes emitting a light pattern in a direction to the surface of the object from a light emitter of the device, the light pattern of a size and shape to indicate a position of the device to a user.

In some embodiments, a method of applying a stretchable electronic device to a surface of an object includes indicating, with a user interface of the device, a position for the stretchable electronic device relative to the surface of the object which includes indicating, with a user interface of the device, that a user should not move the stretchable electronic device relative to the surface of the object. For example, a positional applicator device for applying a stretchable electronic device to a surface of an object can include a "stop" or "hold" light that can be illuminated when the device is in the correct position for application to an adjacent surface. In some embodiments, a method of applying a stretchable electronic device to a surface of an object includes indicating, with a user interface of the device, a position for the stretchable electronic device relative to the surface of the object which includes indicating, with a user interface of the device, a direction that a user should move the stretchable electronic device relative to the surface of the object. For example, a positional applicator device for applying a stretchable electronic device to a surface of an object can include a "left" or "right" light that can be illuminated when the device is not in the correct position for application to an adjacent surface. In some embodiments, a method of applying a stretchable electronic device to a surface of an object includes indicating, with a user interface of the device, a position for the stretchable electronic device relative to the surface of the object which includes indicating, with a user interface of the device, a distance that a user should move the stretchable electronic device relative to the surface of the object. For example, a positional applicator device for applying a stretchable electronic device to a surface of an object can include a user interface that can display a distance such as "2 cm" or "0.5 cm" as needed to position the device in the correct position for application of a stretchable electronic device to an adjacent surface. In some embodiments, a method of applying a stretchable electronic device to a surface of an object includes indicating, with a user interface of the device, a position for the stretchable electronic device relative to the surface of the object which includes indicating, with a user interface of the device, a rotation direction that a user should move the stretchable electronic device relative to the surface of the object. In some embodiments, a method of applying a stretchable electronic device to a surface of an object includes indicating, with a user interface of the device, a position for the stretchable electronic device relative to the surface of the object which includes indicating, with a user interface of the device, a rotation amount that a user should move the stretchable electronic device relative to the surface of the object.

In some embodiments, a method of applying a stretchable electronic device to a surface of an object includes applying the stretchable electronic device to the surface of the object and the applying includes applying tension to the stretchable electronic device from an adaptable tensioner in response to the controller. In some embodiments, a method of applying a stretchable electronic device to a surface of an object includes applying the stretchable electronic device to the surface of the object and the applying includes positioning a surface of the stretchable electronic device against the surface of the object. For example, a positional applicator device for applying a stretchable electronic device can include one or more motors to position the stretchable electronic device relative to the surface and subsurface features of the object. For example, a positional applicator device for applying a stretchable electronic device can include one or more indicators to show a user where to position the stretchable electronic device relative to the surface and subsurface features of the object.

In some embodiments, a method of applying a stretchable electronic device to a surface of an object also includes storing, in electronic memory, data from the detected signal. In some embodiments, a method of applying a stretchable electronic device to a surface of an object also includes storing, in electronic memory, information regarding features of the object. In some embodiments, a method of applying a stretchable electronic device to a surface of an object also includes storing, in electronic memory, information regarding subsurface features of the object. In some embodiments, a method of applying a stretchable electronic device to a surface of an object also includes: detecting, with an accelerometer of the device, a motion of the device; and indicating, with a user interface of the device, in response to the motion of the device. In some embodiments, a method of applying a stretchable electronic device to a surface of an object also includes spraying the surface of the object with an adhesive formulated to adhere a surface of the stretchable electronic device to the surface of the object. In some embodiments, a method of applying a stretchable electronic device to a surface of an object also includes: selecting a portion of the surface of the object in response to the representation of features of the object; and removing the portion of the surface of the object with an abrader of the device. In some embodiments, a method of applying a stretchable electronic device to a surface of an object also includes: determining a light pattern to project on the surface of the object relative to the position of the device; and projecting the light pattern on the surface of the object. In some embodiments, a method of applying a stretchable electronic device to a surface of an object also includes emitting a verbal signal in response to the controller.

FIG. 10 shows aspects of a method of applying a stretchable electronic device to a surface of an object with a positional applicator device. Box 1000 depicts that the method is a method of applying a stretchable electronic device to a surface of an object. Box 1010 illustrates that the method includes retaining a stretchable electronic device with a holder of a device. Box 1020 shows initiating a signal from a signal emitter of the device, the signal directed to a surface of an object. Box 1030 depicts detecting, with a signal receiver of the device, a return signal from the emitted signal. Box 1040 illustrates comparing, with circuitry of the device, the initiated signal and the received return signal. Box 1050 shows forming, in circuitry of the device, a representation of features of the object based on the comparison. Box 1060 illustrates comparing, in circuitry of the device, a representation of features of the stretchable electronic device with the formed representation of features of the object based on the comparison. Box 1070 depicts indicating, with a user interface of the device, a position for the stretchable electronic device relative to the surface of the object. Box 1080 illustrates applying the stretchable electronic device to the surface of the object.

FIG. 11 illustrates optional aspects of the method shown in FIG. 10. Optional box 1100 shows that, in some embodiments, box 1020 includes initiating an optical signal directed to the surface of the object. Optional box 1110 depicts that, in some embodiments, box 1020 includes initiating an ultrasound signal directed to the surface of the object.

FIG. 12 shows optional aspects of the method shown in FIG. 10. Optional box 1200 depicts that, in some embodiments, box 1020 includes initiating an RF signal directed to the surface of the object. Optional box 1210 illustrates that, in some embodiments, box 1020 includes initiating a signal from a signal emitter at a time to create a return signal from the surface of the object wherein the return signal is positioned to be received by the signal receiver of the device.

FIG. 13 depicts optional aspects of the method shown in FIG. 10. Optional box 1300 shows that, in some embodiments, box 1030 includes detecting an optical signal directed from the surface of the object. Optional box 1310 depicts that, in some embodiments, box 1030 includes detecting an ultrasound signal directed from the surface of the object. Optional box 1320 illustrates that, in some embodiments, box 1030 includes detecting an RF signal directed from the surface of the object.

FIG. 14 illustrates optional aspects of the method shown in FIG. 10. Box 1400 depicts that, in some embodiments, box 1040 includes: forming, in circuitry of the positional applicator device, a representation of features of the object; and comparing, in circuitry of the positional applicator device, the representation of features of the object with a representation of features of the stretchable electronic device.

FIG. 15 depicts optional aspects of the method illustrated in FIG. 10. Optional box 1500 shows that, in some embodiments, box 1050 includes providing, from electronic memory of the positional applicator device, information regarding features of the object. Optional box 1510 illustrates that, in some embodiments, box 1050 includes providing, from electronic memory of the positional applicator device, information regarding at least one prior stretchable electronic device that was previously affixed to the surface. For example, the provided information can include one or more of: identification model or code; size, shape and position; adhesive used in the prior application; and/or time duration since the prior application.

FIG. 16 shows optional aspects of the method illustrated in FIG. 10. Optional box 1600 shows that, in some embodiments, box 1060 includes providing, from electronic memory of the positional applicator device, information regarding features of the stretchable electronic device. For example, information regarding features of the stretchable electronic device can include one or more of: number, size, position and type of features; identification model or code; and/or suggested adhesive for use with the stretchable electronic device.

FIG. 17 illustrates optional aspects of the method shown in FIG. 10. Box 1700 depicts that, in some embodiments, box 1070 includes indicating a visual representation of a user interface. FIG. 17 depicts that, in some embodiments, box 1070 includes box 1710, initiating a signal from a sound emitter. Also shown is that, in some embodiments, box 1070 includes box 1720, emitting a light pattern in a direction to the surface of the object from a light emitter of the positional applicator device, the light pattern of a size and shape to indicate a position of the positional applicator device to a user.

FIG. 18 depicts optional aspects of the method shown in FIG. 10. In some embodiments, box 1070 includes box 1800, indicating that a user should not move the stretchable electronic device relative to the surface of the object. FIG. 18 depicts that, in some embodiments, box 1070 includes box 1810, indicating that a user should move the stretchable electronic device relative to the surface of the object. FIG. 18 shows that, in some embodiments, box 1070 includes box 1820, indicating a distance that a user should move the stretchable electronic device relative to the surface of the object.

FIG. 19 illustrates optional aspects of the method shown in FIG. 10. Box 1900 depicts that, in some embodiments, box 1070 includes indicating a rotation direction that a user should move the stretchable electronic device relative to the surface of the object. Box 1910 shows that, in some embodiments, box 1070 includes indicating a rotation amount that a user should move the stretchable electronic device relative to the surface of the object.

FIG. 20 shows optional aspects of the method shown in FIG. 10. Box 2000 depicts that, in some embodiments, box 1080 includes applying tension to the stretchable electronic device from an adaptable tensioner in response to the controller. For example, a controller of a positional applicator device can be configured to send control signals to an adaptable tensioner of the device. FIG. 20 also shows that, in some embodiments, box 1080 includes box 2010, positioning a surface of the stretchable electronic device against the surface of the object. For example, in some embodiments, a positional applicator device can include motors oriented to move a holder and affixed stretchable electronic device to a surface of an adjacent object.

FIG. 21 depicts optional aspects of the method shown in FIG. 10. Box 2100 depicts that, in some embodiments, the method includes storing, in electronic memory, data from the detected signal. Box 2110 illustrates storing, in electronic memory, information regarding features of the object. Box 2120 shows: detecting, with an accelerometer of the device, a motion of the positional applicator device; and indicating, with a user interface of the positional applicator device, in response to the motion of the positional applicator device.

FIG. 22 illustrates optional aspects of the method shown in FIG. 10. Box 2200 shows that, in some embodiments, the method includes spraying, from a positional applicator, the surface of the object with an adhesive formulated to adhere a surface of the stretchable electronic device to the surface of the object. Box 2210 depicts the method steps of: selecting a portion of the surface of the object in response to the representation of features of the object; and removing the portion of the surface of the object with an abrader of the positional applicator device.

FIG. 23 shows optional aspects of the method shown in FIG. 10. Box 2300 depicts that, in some embodiments, the method steps include: determining a light pattern to project on the surface of the object relative to the position of the positional applicator device; and projecting the light pattern on the surface of the object. Box 2310 shows that, in some embodiments, the method steps include emitting a verbal signal in response to the controller. For example, in some embodiments a controller of a positional applicator device can be configured to send control signals to a verbal signal emitter of the positional applicator device.

FIG. 24 depicts aspects of a method of applying a stretchable electronic device to a surface of a body region with a positional applicator device. Box 2400 shows that it is a method of applying a stretchable electronic device to a surface of a body region. Box 2410 depicts retaining a stretchable electronic device with a holder of a positional applicator device. Box 2420 illustrates initiating a signal from a signal emitter of the positional applicator device, the signal directed to a surface of a body region. Box 2430 shows detecting, with a signal receiver of the positional applicator device, a return signal from the emitted signal. Box 2440 illustrates comparing, with circuitry of the device, the initiated signal and the received return signal. Box 2450 shows forming, in circuitry of the positional applicator device, a representation of features of the body region based on the comparison. Box 2460 depicts indicating, with a user interface of the positional applicator device, a position for the stretchable electronic device relative to the surface of the body region. Box 2470 illustrates applying the stretchable electronic device to the surface of the body region.

FIG. 25 depicts aspects of a method of applying a stretchable electronic device to a surface of an inanimate object with a positional applicator device. Box 2500 shows that it is a method of applying a stretchable electronic device to a surface of an inanimate object. Box 2510 depicts retaining a stretchable electronic device with a holder of a positional applicator device. Box 2520 shows initiating a signal from a signal emitter of the positional applicator device, the signal directed to a surface of an inanimate object. Box 2530 illustrates detecting, with a signal receiver of the positional applicator device, a return signal from the emitted signal. Box 2540 shows comparing, with circuitry of the positional applicator device, the initiated signal and the received return signal. Box 2550 depicts forming, in circuitry of the positional applicator device, a representation of features of the inanimate object based on the comparison. Box 2560 shows indicating, with a user interface of the positional applicator device, a position for the stretchable electronic device relative to the surface of the inanimate object. Box 2570 illustrates applying the stretchable electronic device to the surface of the inanimate object.

The state of the art has progressed to the point where there is little distinction left between hardware, software (e.g., a high-level computer program serving as a hardware specification), and/or firmware implementations of aspects of systems; the use of hardware, software, and/or firmware is generally (but not always, in that in certain contexts the choice between hardware and software can become significant) a design choice representing cost vs. efficiency tradeoffs. There are various vehicles by which portions of the processes and/or systems and/or other technologies described herein can be effected (e.g., hardware, software (e.g., a high-level computer program serving as a hardware specification), and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software (e.g., a high-level computer program serving as a hardware specification) implementation; or, yet again alternatively, the implementer may opt for some combination of hardware, software (e.g., a high-level computer program serving as a hardware specification), and/or firmware in one or more machines, compositions of matter, and articles of manufacture. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Optical aspects of implementations will typically employ optically-oriented hardware, software (e.g., a high-level computer program serving as a hardware specification), and or firmware.

In some implementations described herein, logic and similar implementations may include computer programs or other control structures. Electronic circuitry, for example, may have one or more paths of electrical current constructed and arranged to implement various functions as described herein. In some implementations, one or more media may be configured to bear a device-detectable implementation when such media hold or transmit device detectable instructions operable to perform as described herein. In some variants, for example, implementations may include an update or modification of existing software (e.g., a high-level computer program serving as a hardware specification) or firmware, or of gate arrays or programmable hardware, such as by performing a reception of or a transmission of one or more instructions in relation to one or more operations described herein. Alternatively or additionally, in some variants, an implementation may include special-purpose hardware, software (e.g., a high-level computer program serving as a hardware specification), firmware components, and/or general-purpose components executing or otherwise invoking special-purpose components. Specifications or other implementations may be transmitted by one or more instances of tangible transmission media as described herein, optionally by packet transmission or otherwise by passing through distributed media at various times.

Alternatively or additionally, implementations may include executing a special-purpose instruction sequence or invoking circuitry for enabling, triggering, coordinating, requesting, or otherwise causing one or more occurrences of virtually any functional operation described herein. In some variants, operational or other logical descriptions herein may be expressed as source code and compiled or otherwise invoked as an executable instruction sequence. In some contexts, for example, implementations may be provided, in whole or in part, by source code, such as C++, or other code sequences. In other implementations, source or other code implementation, using commercially available and/or techniques in the art, may be compiled/implemented/translated/converted into a high-level descriptor language (e.g., initially implementing described technologies in C or C++ programming language and thereafter converting the programming language implementation into a logic-synthesizable language implementation, a hardware description language implementation, a hardware design simulation implementation, and/or other such similar mode(s) of expression). For example, some or all of a logical expression (e.g., computer programming language implementation) may be manifested as a Verilog-type hardware description (e.g., via Hardware Description Language (HDL) and/or Very High Speed Integrated Circuit Hardware Descriptor Language (VHDL)) or other circuitry model which may then be used to create a physical implementation having hardware (e.g., an Application Specific Integrated Circuit).

In a general sense, various embodiments described herein can be implemented, individually and/or collectively, by various types of electro-mechanical systems having a wide range of electrical components such as hardware, software (e.g., a high-level computer program serving as a hardware specification), firmware, and/or virtually any combination thereof and a wide range of components that may impart mechanical force or motion such as rigid bodies, spring or torsional bodies, hydraulics, electro-magnetically actuated devices, and/or virtually any combination thereof. Consequently, as used herein "electro-mechanical system" includes, but is not limited to, electrical circuitry operably coupled with a transducer (e.g., an actuator, a motor, a piezoelectric crystal, a Micro Electro Mechanical System (MEMS), etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), electrical circuitry forming a communications device (e.g., a modem, communications switch, optical-electrical equipment, etc.), and/or any non-electrical analog thereto, such as optical or other analogs (e.g., graphene based circuitry). Examples of electro-mechanical systems include but are not limited to a variety of consumer electronics systems, medical devices, as well as other systems such as motorized transport systems, factory automation systems, security systems, and/or communication/computing systems. Electro-mechanical, as used herein, is not necessarily limited to a system that has both electrical and mechanical actuation except as context may dictate otherwise.

In a general sense, various aspects described herein can be implemented, individually and/or collectively, by a wide range of hardware, software (e.g., a high-level computer program serving as a hardware specification), firmware, and/or any combination thereof, and can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), and/or electrical circuitry forming a communications device (e.g., a modem, communications switch, optical-electrical equipment, etc.). The subject matter described herein may be implemented in an analog or digital fashion or some combination thereof.

In an embodiment, the system is integrated in such a manner that the system operates as a unique system configured specifically for function of the positional applicator device for applying a stretchable electronic device to a surface of an object, and any associated computing devices of the system operate as specific use computers for purposes of the claimed system, and not general use computers. In an embodiment, at least one associated computing device of the system operate as specific use computers for purposes of the claimed system, and not general use computers. In an embodiment, at least one of the associated computing devices of the system are hardwired with a specific ROM to instruct the at least one computing device. In an embodiment, one of skill in the art recognizes that the positional applicator device for applying a stretchable electronic device to a surface of an object and system effects an improvement at least in the technological field of stretchable electronic devices.

At least a portion of the devices and/or processes described herein can be integrated into a data processing system. A data processing system generally includes one or more of a system unit housing, a video display device, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), and/or control systems including feedback loops and control motors (e.g., feedback for sensing position and/or velocity; control motors for moving and/or adjusting components and/or quantities). A data processing system may be implemented utilizing suitable commercially available components, such as those typically found in data computing/communication and/or network computing/communication systems.

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

The foregoing specification has been described with reference to various embodiments. However, one of ordinary skill in the art will appreciate that various modifications and changes can be made without departing from the scope of the present disclosure. Accordingly, this disclosure is to be regarded in an illustrative rather than a restrictive sense, and all such modifications are intended to be included within the scope thereof. Likewise, benefits, other advantages, and solutions to problems have been described above with regard to various embodiments. However, benefits, advantages, solutions to problems, and any element(s) that may cause any benefit, advantage, or solution to occur or become more pronounced are not to be construed as a critical, a required, or an essential feature or element. As used herein, the terms "comprises," "comprising," and any other variation thereof are intended to cover a non-exclusive inclusion, such that a process, a method, an article, or an apparatus that comprises a list of elements does not include only those elements but may include other elements not expressly listed or inherent to such process, method, system, article, or apparatus.

All of the above U.S. patents, U.S. patent application publications, U.S. patent applications, foreign patents, foreign patent applications and non-patent publications referred to in this specification and/or listed in any Application Data Sheet, are incorporated herein by reference, to the extent not inconsistent herewith.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A positional applicator device for applying a stretchable electronic device to a surface of an object, comprising:
    a holder for a stretchable electronic device;
    a signal emitter positioned to direct an emitted signal toward a surface of an object;
    a receiver positioned to detect a return signal from the surface of the object;
    circuitry operably connected to the signal emitter and the receiver, the circuitry configured to compare the emitted signal with the return signal in order to identify surface and subsurface features of the object;
    circuitry configured to compare the identified surface and subsurface features with a map of surface and subsurface features of the object stored in memory; and
    a positioner operably affixed to the holder, the positioner positioned and structured to apply the stretchable electronic device to a position on the surface of the object based on the comparison of the identified surface and subsurface features with a map of surface and subsurface features of the object stored in memory.

2. A positional applicator device for applying a stretchable electronic device to a surface of an object, comprising:
    a holder for a stretchable electronic device;
    a signal emitter positioned to direct an emitted signal toward a surface of an object;
    a signal receiver positioned to detect a return signal from the surface of the object, the return signal originating with the emitted signal directed from the signal emitter;
    a controller including circuitry operably connected to the signal emitter and to the signal receiver, the circuitry configured to compare the emitted signal with the return signal to form a representation of features of the object, and circuitry configured to compare the representation of features of the object with a representation of features of the stretchable electronic device;
    a user interface operably attached to the controller;
    a positioner operably affixed to the holder, the positioner positioned and structured to apply, in response to the controller, the stretchable electronic device to a position on the surface of the object relative to the representation of features of the object and the representation of features of the stretchable electronic device; and
    an applicator of a size and shape to place the stretchable electronic device in contact with the surface of the object, the applicator including a switch operably attached to the controller.

3. The positional applicator device of claim 2, wherein the holder comprises:
    a reel of a size and shape to hold at least one stretchable electronic device; and
    a motor operably attached to the reel.

4. The positional applicator device of claim 2, wherein the holder comprises:
    a manipulator positioned to alter the size of the stretchable electronic device.

5. The positional applicator device of claim 2, wherein the holder comprises:
    an adaptable tensioner of a size, shape and position to control tension of the stretchable electronic device.

6. The positional applicator device of claim 2, wherein the controller comprises:
    electronic memory including information regarding features of the object.

7. The positional applicator device of claim 2, wherein the controller comprises:
    electronic memory including information regarding features of the stretchable electronic device.

8. The positional applicator device of claim 2, wherein the positioner comprises:
    at least one fastener affixed to the holder; and
    a motor attached to the fastener, the motor operably attached to the controller.

9. The positional applicator device of claim 2, wherein the applicator comprises:
    an adaptable tensioner of a size, shape and position to control tension of the stretchable electronic device during application.

10. The positional applicator device of claim 2, further comprising:
    a sprayer positioned to apply material to the surface of the object; and
    a reservoir operably attached to the sprayer.

11. The positional applicator device of claim 2, further comprising:
    a gas blower positioned to direct gas to the surface of the object; and a switch affixed to the gas blower, the switch responsive to the controller.

12. The positional applicator device of claim 2, further comprising:
an abrader of a size and shape to remove a portion of the surface of the object;
a holder affixed to the abrader;
a positioner affixed to the abrader, the positioner oriented to position the abrader relative to the surface of the object.

13. The positional applicator device of claim 2, further comprising:
one or more projections positioned and oriented to contact the surface of the object; and
one or more adaptable tensioners affixed to the one or more projections and responsive to the tension of the surface.

14. The positional applicator device of claim 2, further comprising:
a light source positioned to direct light in a visible pattern toward the surface of the object.

15. A positional applicator device for applying a stretchable electronic device to a surface of a body region, comprising:
a holder for a stretchable electronic device;
a signal emitter positioned to direct an emitted signal toward a surface of a body region;
a signal receiver positioned to detect a return signal from the surface, the return signal originating with the emitted signal directed from the signal emitter;
a controller including circuitry operably connected to the signal emitter and the signal receiver, the circuitry configured to compare the emitted signal with the return signal to form a representation of features of the body region, and circuitry configured to compare the representation of features of the body region with a representation of features of the stretchable electronic device;
a user interface operably attached to the controller;
a positioner operably affixed to the holder, the positioner positioned and structured to apply, in response to the controller, the stretchable electronic device to a position on the surface of the body region based on information obtained from the representation of features of the body region and the representation of features of the stretchable electronic device; and
an applicator of a size and shape to place the stretchable electronic device in contact with the surface of the body region, the applicator including a switch operably attached to the controller.

16. The positional applicator device of claim 15, wherein the holder comprises:
a manipulator positioned to alter the size of the stretchable electronic device.

17. The positional applicator device of claim 15, wherein the holder comprises:
an adaptable tensioner of a size, shape and position to control tension of the stretchable electronic device.

18. The positional applicator device of claim 15, wherein the signal receiver is of a type to detect an emitted signal originating from the signal emitter and reflected from the surface of the body region.

19. The positional applicator device of claim 15, wherein the controller comprises:
electronic memory including information regarding features of the stretchable electronic device.

20. The positional applicator device of claim 15, wherein the positioner comprises:
at least one fastener affixed to the holder; and
a motor attached to the fastener, the motor operably attached to the controller.

21. The positional applicator device of claim 15, wherein the applicator comprises:
an adaptable tensioner of a size, shape and position to control tension of the stretchable electronic device during application to the surface of the body region.

22. The positional applicator device of claim 15, further comprising:
a sprayer positioned to apply material to the surface of the body region; and
a reservoir operably attached to the sprayer.

23. The positional applicator device of claim 15, further comprising:
a gas blower positioned to direct gas to the surface of the body region; and
a switch affixed to the gas blower, the switch responsive to the controller.

24. The positional applicator device of claim 15, further comprising:
an abrader of a size and shape to remove a portion of the surface of the body region;
a holder affixed to the abrader;
a positioner affixed to the abrader, the positioner oriented to position the abrader relative to the surface of the body region.

25. The positional applicator device of claim 15, further comprising:
one or more projections positioned and oriented to contact the surface of the body region; and
one or more adaptable tensioners affixed to the one or more projections and responsive to the tension of the surface of the body region.

26. The positional applicator device of claim 15, further comprising:
a light source positioned to direct light in a visible pattern toward the surface of the body region.

27. A positional applicator device for applying a stretchable electronic device to a surface of an inanimate object, comprising:
a holder for a stretchable electronic device;
a signal emitter positioned to direct an emitted signal toward a surface of an inanimate object;
a signal receiver positioned to detect a return signal from the surface, the return signal originating with the emitted signal directed from the signal emitter;
a controller including circuitry operably connected to the signal emitter and the signal receiver, the circuitry configured to compare the emitted signal with the return signal to form a representation of features of the inanimate object, and circuitry configured to compare the representation of features of the inanimate object with a representation of features of the stretchable electronic device;
a user interface operably attached to the controller;
a positioner operably affixed to the holder, the positioner positioned and structured to apply, in response to the controller, the stretchable electronic device to a position on the surface of the inanimate object based on information obtained from the representation of features of the inanimate object and the representation of features of the stretchable electronic device; and
an applicator of a size and shape to place the stretchable electronic device in contact with the surface of the inanimate object, the applicator including a switch operably attached to the controller.

28. The positional applicator device of claim 27, wherein the holder comprises:
a manipulator positioned to alter the size of the stretchable electronic device.

29. The positional applicator device of claim 27, wherein the holder comprises:
an adaptable tensioner of a size, shape and position to control tension of the stretchable electronic device.

30. The positional applicator device of claim 27, wherein the controller comprises:
electronic memory including information regarding features of the inanimate object.

31. The positional applicator device of claim 27, wherein the controller comprises:
electronic memory including information regarding features of the stretchable electronic device.

32. The positional applicator device of claim 27, wherein the positioner comprises:
at least one fastener affixed to the holder; and
a motor attached to the fastener, the motor operably attached to the controller.

33. The positional applicator device of claim 27, wherein the applicator comprises:
an adaptable tensioner of a size, shape and position to control tension of the stretchable electronic device during application.

34. The positional applicator device of claim 27, further comprising:
a sprayer positioned to apply material to the surface of the inanimate object; and
a reservoir operably attached to the sprayer.

35. The positional applicator device of claim 27, further comprising:
a gas blower positioned to direct gas to the surface of the inanimate object; and
a switch affixed to the gas blower, the switch responsive to the controller.

36. The positional applicator device of claim 27, further comprising:
an abrader of a size and shape to remove a portion of the surface of the inanimate object;
a holder affixed to the abrader;
a positioner affixed to the abrader, the positioner oriented to position the abrader relative to the surface of the inanimate object.

37. The positional applicator device of claim 27, further comprising:
one or more projections positioned and oriented to contact the surface of the inanimate object; and
one or more adaptable tensioners affixed to the one or more projections and responsive to the tension of the surface of the inanimate object.

38. The positional applicator device of claim 27, further comprising:
a light source positioned to direct light in a visible pattern toward the surface of the inanimate object.

* * * * *